US005512421A

United States Patent [19]

Burns et al.

[11] Patent Number: 5,512,421
[45] Date of Patent: Apr. 30, 1996

[54] GENERATION, CONCENTRATION AND EFFICIENT TRANSFER OF VSV-G PSEUDOTYPED RETROVIRAL VECTORS

[75] Inventors: Jane C. Burns, La Jolla; Jiing-Kuan Yee, Del Mar; Theodore Friedmann, La Jolla, all of Calif.

[73] Assignee: The Regents of the University of California, Oakland, Calif.

[21] Appl. No.: 104,804

[22] Filed: Aug. 10, 1993

Related U.S. Application Data

[63] Continuation-in-part of Ser. No. 73,209, Jun. 4, 1993, abandoned, which is a continuation-in-part of Ser. No. 740,766, Aug. 8, 1991, abandoned, which is a continuation-in-part of Ser. No. 658,632, Feb. 19, 1991, abandoned.

[51] Int. Cl.$^6$ .............................. C12N 15/86; C12N 7/02; C12N 15/47; C12N 15/48
[52] U.S. Cl. ...................... 435/320.1; 424/93.2; 435/239; 935/32
[58] Field of Search ................................ 435/235.1, 239, 435/320.1

[56] References Cited

FOREIGN PATENT DOCUMENTS

| 0243204 | 10/1987 | European Pat. Off. . |
|---|---|---|
| WO/8901516 | 2/1989 | WIPO . |
| WO/9005538 | 5/1990 | WIPO . |
| WO/9012087 | 10/1990 | WIPO . |
| WO/9015141 | 12/1990 | WIPO . |
| WO/9102805 | 3/1991 | WIPO . |
| WO/9106658 | 5/1991 | WIPO . |
| WO/9205266 | 4/1992 | WIPO . |

OTHER PUBLICATIONS

J. C. Burns et al. (1993) Proc. Natl. Acad. Sci. USA 90: 8033–8037.
N. Hopkins (1993) Proc. Natl. Acad. Sci. USA 90:8759–8760.
J.-K. Yee et al. (1994) Methods in Cell Biology 43:99–112.
J.-K. Yee et al. (1994) Proc. Natl. Acad. Sci. USA 91:9564–9568.
Graham et al. Virology, 52:456–457 (1973).
Jolly et al. Mol. Cell Biol., 6:1141–1145 (1986).
Li et al. Virology, 171:331–341 (1989).
Littlefield et al. Nature, 211:250–252 (1966).
Miller et al. Mol. Cell Biol., 5:431–437 (1985).
Miller et al. Science, 225:630–632 (1984).
Okayama et al. Mol Cell Biol. 3:280–289 (1983).
Quade et al. Virology, 98:461–465 (1979).
Rose et al. Cell, 30:753–762 (1982).
Rose et al. J. Virol., 39:519–528 (1981).
Vaux et al. Nature, 336:36–42 (1988).
Adam et al. J. Virol. 62(10):3802–3806 (1988).
Ban et al. J. Gen. Virol., 70:1987–1993 (1989).
Baskin, Yvonne *The Gene Doctors, Medical Genetics at the Frontier*, William Morrow & Co. N.Y. p. 211 (1984).
Bender et al. J. Virology, 61:1639–1646 (1987).
Besmer et al. J. Virol., 21(3):965–973 (1977).

(List continued on next page.)

*Primary Examiner*—Jacqueline M. Stone
*Assistant Examiner*—Johnny F. Railey, II
*Attorney, Agent, or Firm*—Knobbe Martens Olson & Bear

[57] ABSTRACT

The present application discloses retrovirus-derived vectors in which the retroviral envelope glycoprotein has been replaced by the G glycoprotein of vesicular stomatitis virus, and the use of these vectors in the transfer of exogenous genes into the cells of a wide variety of non-mammalian organisms. Also disclosed is a method for the generation of retroviral vectors in high titers, wherein a recombinant, stable host cell line is provided which harbors the retroviral vector of interest without envelope protein. High-titer retroviral vector production is initiated by introducing nucleic acid encoding a functional membrane-associated protein into the cell line. The vectors disclosed in the present application can be concentrated by ultracentrifugation to titers greater than $10^9$ cfu/ml which are especially useful in human gene therapy trials, and can also infect cells, such as hamster and fish cells, that are ordinarily resistant to infection with vectors containing the retroviral envelope protein.

7 Claims, 10 Drawing Sheets

OTHER PUBLICATIONS

Cone, Robert et al. Proc. Ntl. Acad. Sci. USA 81:6349–6353 (1988).
Danos et al. Proc Natl. Acad. Sci, USA 85:6460–6464 (1988).
Delouis et al. Biochem. Biophys. Res. Comm. 169(1):8–14 (1990).
Embretson et al. J. Virology 60(2):662–668 (1986).
Embretson et al. J. Virology 61:2675–2683 (1987).
Hoshino et al. Int. J. Cancer, 36:671–675 (1985).
Huang, A. S. et al. J. Virology, 12:659–662 (1973).
Livingston et al. Virology, 70:432–4390 (1976).
Love et al. Virology, 57:217–278 (1974).
Mann et al. Cell, 33:153–159 (1983).
Markowitz et al. J. Virology, 62(4):1120–1124 (1988).
Markowitz et al. Virology, 167:400–406 (1988).
Miller et al. Human Gene Therapy, 1:5–15 (1990).
Miller et al. Mol. Cell Biol, 6(8):2895–2902 (1986).
Mohr et al. Virology, 117:522–529 (1982).
Morgenstern et al. Nucl. Acids Res., 18:3587–3596 (1990).
Schlegel et al. Cell, 32:639–646 (1983).
Schnitzer et al. J. Virology 23(3):449–454 (1977).
Sorge et al. Mol. Cell Biol, 4(9):1730–1737 (1984).
Tato et al. Virology 88:71–81 (1978).
Watanabe et al. Mol. Cell Biol. 3: 2241–2249 (1983).
Watanabe et al. Proc. Natl. Acad. Sci., USA 79–5986–5990 (1982).
Weiss et al. Virology, 100:252–274 (1980).
Whitt et al. J. Virology, 63:3569–3578 (1989).
Willey et al. J. Virology 62:139–147 (1988).
Wills et al. J. Cell Biol. 99:2011–2023 (1984).
Wilson et al. J. Virology, 63:2374–2378 (1989).
Witte et al. Cell, 11:505–511 (1977).
Zavada, J. J. Gen Virol., 125:183–191 (1972).
Zavada et al. Acta Virol., 27:110–118 (1983).
N. Emi et al. J. Cell. Biochem. Suppl, 14 A:367, Abstract D408.
J. W. Wills Nature 340:323–324 (1989).
J. R. McLachlin et al. Prog. Nucl. Acid Res. and Mol. Biol. 38:91–134 (1990).
L. M. Roman et al. Experimental Cell Research 175:376–387 (1988).
Young et al., "Efficient Incorporation of Human CD4 Protein into Avian Leukosis Virus Particles," Science, 250:1421–1423 (1990).

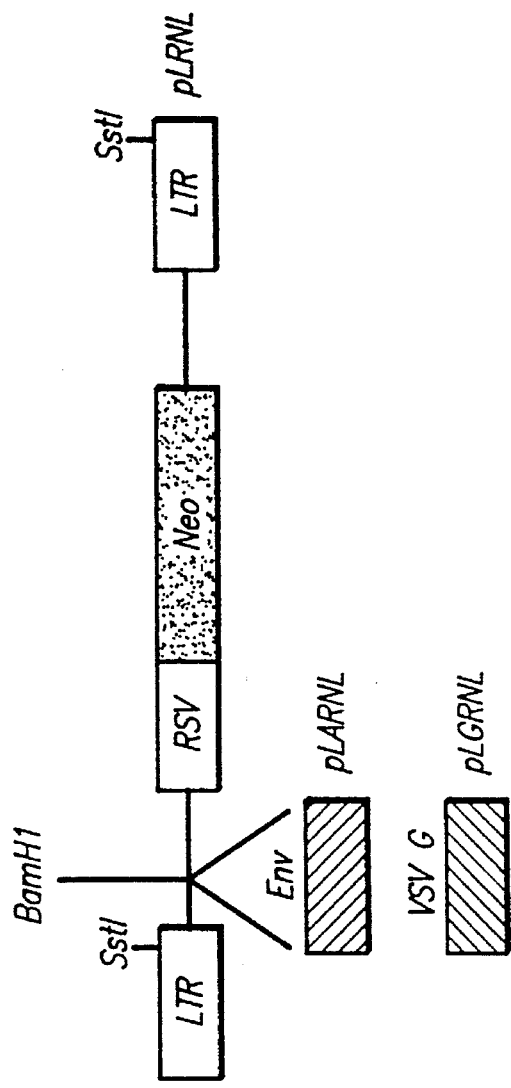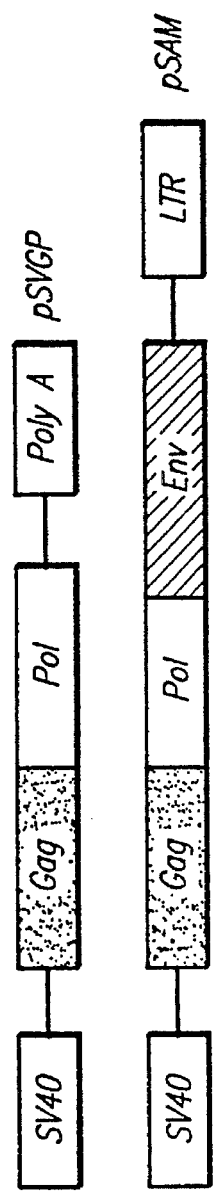
FIG. 1(A)
FIG. 1(B)

| CELL LINE | LSPONL (GO) | LSPONL (A) |
|---|---|---|
| 208F | $1.2 \times 10^6$ | $8.2 \times 10^5$ |
| HeLa | $4.6 \times 10^5$ | $1.0 \times 10^5$ |
| gHTEO | $2.2 \times 10^6$ | $5.0 \times 10^5$ |
| Basinger | $5.0 \times 10^4$ | $1.2 \times 10^5$ |
| TO-119 | $1.0 \times 10^4$ | $1.5 \times 10^4$ |
| 208F | $3.0 \times 10^6$ | $6.0 \times 10^5$ |
| U251 | $1.0 \times 10^6$ | $6.0 \times 10^4$ |
| U-138 | $2.0 \times 10^5$ | $8.0 \times 10^4$ |
| Hs883 | $2.0 \times 10^5$ | $4.0 \times 10^4$ |
| U373MG | $9.0 \times 10^5$ | $1.0 \times 10^5$ |
| LNZ-E8 | $2.0 \times 10^5$ | N.D. |

GENERATION, CONCENTRATION AND EFFICIENT TRANSFER OF VSV-G PSEUDOTYPED RETROVIRAL VECTORS

GOVERNMENT INTEREST IN INVENTION

Certain aspects of the invention disclosed herein were made with government support under U.S. Public Health Service grants HD20034 and AI28945 from the National Institutes of Health. The government has certain rights in these aspects of the invention.

RELATED APPLICATIONS

The present application is a continuation in part of co-pending United States patent application Ser. No. 073,209, filed Jun. 4, 1993, now abandoned, which is a continuation-in-part of United States patent application Ser. No. 740,766, filed Aug. 8, 1991, now abandoned, which is a continuation-in-part of United States patent application Ser. No. 658,632, filed Feb. 19, 1991 now abandoned. The disclosures of these previous applications are hereby incorporated by reference.

FIELD OF THE INVENTION

The present invention relates generally to the field of viral vectors having an altered host range. More specifically, the present invention relates to the generation of high-titer pseudotyped retroviral vectors.

BACKGROUND OF THE INVENTION

The assembly of enveloped animal viruses is characterized by selective inclusion of the viral genome and accessory viral proteins into a budding viral particle. Although the mechanisms for selective encapsidation or packaging are not well characterized, it has been postulated that the recognition of viral envelope proteins within the plasma membrane by the viral nucleocapsids represents one probable control point for packaging specificity.

Using internal image anti-idiotype antibodies, Vaux et al. (Nature (London) 336:36–42 (1988)) have shown that the nucleocapsid of Semliki Forest virus (SFV) contains a specific receptor for the cytoplasmic tail of the virion E2 spike glycoprotein. Vaux et al. suggested that a specific receptor-ligand-like interaction between the two is likely to be critical in the organization of the budding of SFV and related viruses from infected cells.

In apparent contrast to the high degree of specificity of SFV for the E2 protein, is the well-known phenomenon of "pseudotype" formation, in which mixed infection of a cell by one virus and retroviruses results in the production of progeny virions bearing the genome of one of the viruses encapsidated by the envelope proteins of the other. These phenotypically mixed viruses form plaques on appropriate indicator cells and can be neutralized by sera raised against the specific envelope protein. One virus known to participate in pseudotype formation is vesicular stomatitis virus (VSV), a member of the rhabdovirus family.

The mechanism for the inclusion of the envelope protein of one virus into the virions of an unrelated virus is uncertain. Sequence comparison of VSV G protein and retrovirus envelope proteins reveals no significant sequence similarity among these proteins. Heretofore, it has also been difficult to determine whether G protein alone in the absence of other VSV-encoded proteins can participate in pseudotype formation. Pseudotypes do not form between VSV and alphaviruses such as SFV even though pseudotypes can form between two alphaviruses or between alphaviruses and related flaviviruses such as Japanese encephalitis virus.

In some cases, phenotypic mixing is unilateral, as in the case of VSV with fowl plaque virus (FPV) or VSV with Sindbis virus. The pseudotype virus particle VSV(FPV) containing the VSV genome encapsidated by the envelope protein of FPV and the pseudotype virus particle VSV(Sindbis) have been demonstrated, but the reverse pseudotypes, FPV(VSV) and Sindbis(VSV), containing FPV or Sindbis virus genome with the VSV G protein, have not been detected.

Mixed infection of cells with retroviruses and VSV usually results in the formation of pseudotypes with much lower titers than that of VSV generated from the same cells. It is not clear whether this is due to the specificity of the interaction between the retroviral nucleocapsid and the G protein or due to other factors.

Retroviral vectors have been used to transfer genes efficiently by exploiting the viral infectious process. Foreign genes cloned into the retroviral genome can be delivered efficiently to cells susceptible to infection by the retrovirus. Through other genetic manipulations, the replicative capacity of the retroviral genome can be destroyed. The vectors introduce new genetic material to a cell but are unable to replicate. A helper virus or a packaging system can be used to permit vector particle assembly and egress. As used herein, the term "vector particle" refers to viral-like particles that are capable of introducing nucleic acid into a cell through a viral-like entry mechanism. Such vector particles, can under certain circumstances, mediate the transfer of genes into the cells they infect.

It is possible to alter the range of cells that these vectors can infect by including an envelope gene from another closely related virus. Miller et al. (Mol. Cell. Biol. 5:431–437 (1985)) constructed a MoMLV-derived vector to introduce a selectable marker, dihydrofolate reductase, into susceptible cells, and included the envelope region from the related amphotropic retrovirus 4070A to broaden the host range of the vector. Other investigators have described pseudotypes of retroviral vectors whose host cell range has been altered by substitution of envelope proteins from different viruses. Substitution of the gibbon ape leukemia virus envelope protein for the amphotropic retroviral envelope has resulted in vectors capable of infecting bovine and hamster cells, species not susceptible to infection with retroviral vectors containing the MoMLV envelope protein (Miller et al, J. Virol., 65:2220–2224 (1991)). Similarly, substitution of the HTLV I envelope protein has been shown to restrict the host cell range of a MoMLV-based vector to cells infectable by HTLV I (Wilson et al., J. Virol., 63:2374–2378, (1989)).

Retroviral vectors derived from Moloney murine leukemia virus (MoMLV) are important tools for stable gene transfer into mammalian cells. They have been used to study gene regulation and expression and to facilitate gene transfer for studies of human gene therapy. Two significant limitations to the use of these retroviral vectors are the restricted host cell range and the inability to produce high-titer virus. Infection with retroviral vectors results from specific interaction of the viral envelope glycoprotein with cellular receptors, defining the host range and determining the efficiency of infection. Attempts to concentrate retroviral vectors by centrifugation or other physical means generally result in loss of infectious virus with only minimal increases in titer. The instability of retroviral particles may be related to structural characteristics of the envelope protein and modification of envelope components might, therefore, result in a more stable particle.

As stated above, it is not clear what signals are required to direct the functional assembly of the vector particle, nor is it known what factors permit the nucleocapsid and the membrane-associated protein to interact and complete packaging. Accordingly, heretofore, alterations in the host range have not been effected by including heterologous membrane-associated proteins within a vector particle. By "heterologous membrane-associated protein" it is meant a membrane-associated protein having at least one origin other than a virus of the same viral family as the origin of the nucleocapsid protein of the vector particle. As used herein, viral "family" shall be used to refer to the taxonomic rank of family, as assigned by the International Committee on Taxonomy of Viruses.

SUMMARY OF THE INVENTION

According to one aspect of the invention, there is provided a method of introducing foreign nucleic acid into a cell of a non-mammalian species. The method includes infecting the cell with a vector particle. The vector particle includes the following components: the foreign nucleic acid, a nucleocapsid encapsidating the nucleic acid, the nucleocapsid comprising nucleocapsid protein of a retrovirus, and a membrane surrounding the nucleocapsid. The membrane has vesicular stomatitis virus (VSV) G protein associated therewith. In a preferred embodiment, the retrovirus is MoMLV. In another preferred embodiment, the nucleic acid sequence is operably linked to a promoter and encodes a gene that is expressible into a polypeptide. In one embodiment, the promoter comprises a tissue-specific promoter. Another embodiment comprises transcribing the nucleic acid sequence into complementary RNA. A further embodiment comprises expressing the polypeptide through translation of the RNA. Preferably, the nucleic acid sequence becomes integrated into the genome of the cell. In another preferred embodiment, the nucleic acid comprises a selectable marker gene. The selectable marker can be a neomycin resistance gene. In other embodiments, the non-mammalian species is a fish such as a zebra fish, an insect such as a mosquito, or an amphibian such as a frog.

According to another aspect of the invention there is provided a method for concentrating vector particles. This aspect of the invention involves growing enveloped vector particles. The particles comprise a nucleocapsid including nucleocapsid protein having an origin from a retrovirus, a nucleic acid sequence encapsidated by the nucleocapsid protein, and a membrane-associated protein which is vesicular stomatitis virus (VSV) G protein. The method also comprises harvesting the vector particles, and concentrating the vector particles to form a pellet containing the viral particles. In preferred embodiments, the concentrating step is ultracentrifugation, filtration or chromatography. A preferred embodiment further comprises resuspending the pellet in a liquid and subjecting it to a second cycle of ultracentrifugation. In a further preferred embodiment, the liquid is TNE or 0.1% Hank's balanced salt solution. In a preferred embodiment of the method, the vector particles are concentrated to a titer of at least $10^8$ cfu/ml or, in a particularly preferred embodiment, to a titer of at least $10^9$ cfu/ml. In another embodiment, the pellet retains over 50% of the colony forming units present prior to ultracentrifugation. In yet another embodiment, the pellet retains over 90% of the colony forming units present prior to ultracentrifugation.

According to another aspect of the invention, there is provided a solution of retroviral particles comprising a titer of at least $10^8$ cfu/ml. In a preferred embodiment, the solution comprises a titer of at least $10^9$ cfu/ml. In one embodiment of the solution, the retroviral particles comprise a membrane-associated protein that is VSV-G protein. In another embodiment of the solution, the retroviral particles comprise MoMLV nucleocapsid protein.

According to yet another aspect of the invention, there is provided a method of introducing foreign nucleic acid into a germ cell of a non-mammalian species. In this aspect of the invention, the method includes exposing embryos of an individual member of the non-mammalian species to a vector particle. The vector particle comprises the foreign nucleic acid, a nucleocapsid encapsidating the nucleic acid, and a membrane surrounding the nucleocapsid. The nucleocapsid comprises nucleocapsid protein of a retrovirus, and the membrane has VSV G protein associated therewith. The method further comprises growing the embryos into adults, breeding the adults to produce an $F_2$ generation, and identifying adults that produce an $F_2$ generation carrying the foreign nucleic acid. The adults contain the foreign nucleic acid in their germ line. In one embodiment of the invention, the retrovirus is MoMLV. In another embodiment, the foreign nucleic acid is operably linked to a promoter and encodes a gene expressible into a polypeptide. The promoter can be a tissue-specific promoter. In a preferred embodiment, the foreign nucleic acid sequence is operably linked to a promoter and encodes a gene that can be transcribed into complementary RNA, and optionally further translated into polypeptide. In one embodiment, the nucleic acid sequence is integrated into the genome of the germ cells.

According to another aspect of the invention, there is provided a method of introducing foreign nucleic acid into a germ cell of a non-mammalian species. This method comprises exposing germ cells of the non-mammalian species to a vector particle. The vector particle comprises the foreign nucleic acid, a nucleocapsid encapsidating the nucleic acid, and a membrane surrounding the nucleocapsid. The nucleocapsid comprises nucleocapsid protein of a retrovirus, and the membrane has VSV G protein associated therewith. The method further comprises implanting the germ cells into embryos of the non-mammalian species, growing the embryos into adults, breeding the adults to produce an $F_2$ generation, and identifying adults that produce an $F_2$ generation carrying the foreign nucleic acid. The adults contain the foreign nucleic acid in their germ line. In a preferred embodiment, the germ cells are identified using an antibody for germ cells of the non-mammalian species.

According to still another aspect of the present invention, there is provided a method for the generation of high-titer retroviral vectors. This method comprises obtaining host cells comprising a first nucleic acid sequence encoding the production of retroviral nucleocapsid protein, and introducing into the host cells a second nucleic acid sequence comprising retroviral long terminal repeats (LTRs) and a desired exogenous gene, thereby creating a recombinant host cell. A third nucleic acid sequence operably linked to a promoter is then introduced into the recombinant host cell. The third nucleic acid sequence encodes a membrane-associated protein having cytoplasmic, transmembrane and extracellular domains. The resulting retroviral particles comprise an envelope with the membrane-associated protein therein and a genome comprising the exogenous gene. In a preferred embodiment, the first nucleic acid sequence includes the retroviral gag and pol genes. In another embodiment, the retrovirus is MoMLV. In yet another preferred embodiment, the second nucleic acid sequence encodes a selectable marker. The selectable marker can be a neomycin resistance gene. In still another embodiment, the desired exogenous gene is expressible into a polypeptide. According to this aspect of the invention, the second nucleic acid sequence can be introduced into the host cells by infecting the host cell with a virus having a genome comprising the second nucleic acid sequence or by transfecting the cell with a plasmid comprising the second nucleic acid sequence. The third nucleic acid sequence can be introduced into the recombinant host cells by infecting the host cell with a virus having a genome comprising the third nucleic acid sequence or by transfecting the cell with a plasmid comprising the third nucleic acid sequence. In a preferred embodiment of the invention, the promoter is derived from the human cytomegalovirus. In another embodiment, the protein is the vesicular stomatitis virus (VSV) G protein. In yet another embodiment, the protein is a non-viral protein, such as CD4 protein. An especially preferred form of this aspect of the present invention further comprises concentrating the retroviral particles. In a preferred embodiment, the concentrating step comprises ultracentrifugation. Another preferred form of this aspect of the invention further comprises infecting cells with the retroviral particles. In one embodiment, the cells are located in a living organism in vivo. In another embodiment, the cells are growing in vitro.

According to still another aspect of the present invention, there is provided a recombinant host cell comprising a first nucleic acid sequence encoding the production of retroviral nucleocapsid protein and a second nucleic acid sequence comprising retroviral long terminal repeats and a desired exogenous gene. In one embodiment, the host cell is a 293GP cell. In another embodiment, the second nucleic acid sequence encodes a selectable marker. The selectable marker can be a neomycin resistance gene. In yet another embodiment, the desired exogenous gene is expressible into a polypeptide.

According to yet another aspect of the present invention, there is provided a method of introducing a desired gene into a cell. This method comprises obtaining a recombinant host cell comprising a first nucleic acid sequence encoding the production of a retroviral nucleocapsid protein, and a second nucleic acid sequence comprising retroviral long terminal repeats and a desired exogenous gene. A vector carrying a gene encoding a membrane-associated protein is introduced into the host cell, producing retroviral particles in the recombinant host cells. These retroviral particles comprise an envelope with the membrane-associated protein therein and a genome comprising the exogenous gene. These retroviral particles are used to infect the cell. The cell can be located in vivo, or alternatively, can be located in vitro. In one embodiment, the first nucleic acid sequence encodes retroviral gag and pol proteins. In another embodiment, the retrovirus is MoMLV. In yet another embodiment, the second nucleic acid sequence encodes a selectable marker. This selectable marker can be a neomycin resistance gene. In a preferred embodiment, the desired exogenous gene is expressible into a polypeptide. In a preferred form of this aspect of the invention, the introducing step comprises infecting the recombinant host cell with a virus or transfecting the recombinant host cell with a plasmid. In a preferred embodiment, the membrane-associated protein is the vesicular stomatitis virus (VSV) G protein. In another embodiment, the membrane-associated protein is a non-viral protein, such as CD4 protein. An especially preferred form of this aspect of the present invention further comprises concentrating the retroviral particles prior to infecting the cell. In a preferred embodiment, the concentrating step comprises ultracentrifugation.

BRIEF DESCRIPTION OF THE FIGURES

FIGS. 1(A) and 1(B) are a schematic representation, not drawn to scale, of retroviral vectors and packaging constructs for the creation of retroviral vector particles pLRNL, pLARNL and pLGRNL are shown in FIG. 1 (A) and pSVGP and pSAM are shown in FIG. 1(B).

FIG. 2 shows a Southern blot analysis of LGRNL infected cells using neomycin resistance gene as probe.

FIG. 10 depicts the G418 resistance titer of the pseudotyped virus LSPONL(G) relative to that of its amphotropic counterpart LSPONL(A) in the rat 208F fibroblast line and various human cell lines.

DETAILED DESCRIPTION OF THE INVENTION

Figure 3:
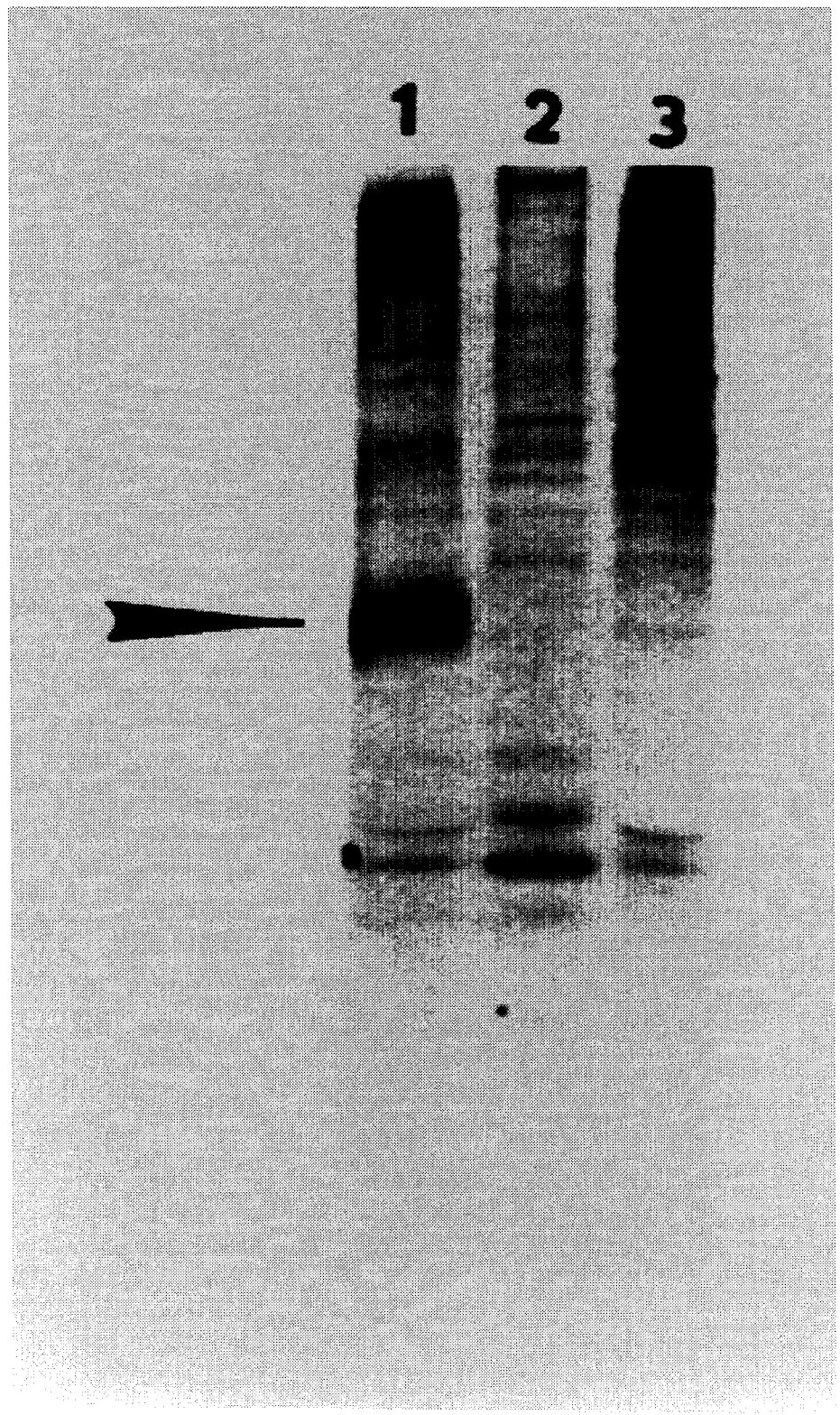
FIG. 3 shows immunoprecipitates separated by SDS-PAGE and visualized by fluorography. Lanes 1 and 2 show the polyclonal cell line immunoprecipitated with anti-VSV G and normal rabbit serum, respectively. Lane 3 is mock infected MDCK cells immunoprecipitated with anti-VSV G antibody.

We have discovered that specific membrane-associated protein from unrelated virus can be incorporated into retroviral vector particles to provide an altered host range throughout a broad spectrum of cells.

As a model system, we incorporated the VSV G membrane-associated protein into Moloney murine leukemia virus (MoMLV)-based vector particles to generate a retroviral vector particle having a nucleocapsid derived from MLV and the membrane associated protein VSV G within its envelope. Such vector particles shall be referred to herein by the designation MLV[VSV G]. This designation shall be used herein generally to refer to vector particles having a nucleocapsid from one viral origin and a membrane-associated protein from another origin, with the non-bracketed portion of the designation referring to the capsid origin and the bracketed portion referring to the membrane-associated protein within the envelope of the vector particle.

For production of vector particles, the nucleic acid of the vector particles of the present invention can be used to transfect a suitable cell line. The vector particles are released into the supernatant from the transfected cells and used to infect a desired cell type. The nucleic acid used for transfection can either be in isolated form or can be already packaged into vector particles. In some instances, a helper virus is required to facilitate virion assembly. Thus, for example, the genes encoding the gag and pol genes can be incorporated into the nucleic acid of a helper virus and functional sequences from another virus can be incorporated into the nucleic acid which is packaged into the vector particles.

The gene encoding a membrane-associated envelope protein can be incorporated within the nucleic acid of either the vector particle or of the helper virus. Alternatively, the gene for this envelope protein could be expressed from a third fragment of nucleic acid or from the genome of the producer cell. In a preferred form of the present invention, the nucleic acid within the vector particle is integrated into the cellular genome of the cell infected by the vector particle, the envelope gene is located on a different fragment of nucleic acid than the nucleic acid that is vector particle genome. Thus, in this preferred embodiment, the membrane-associated protein will not be produced by the vector particle infected cells containing the integrated nucleic acid from the vector particle.

As will be described hereinbelow, we have discovered that the VSV G protein alone is sufficient to interact with the nucleocapsid of MoMLV in the formation of MLV[VSV G] vector particles. The process of incorporation of the VSV G protein into the vector particles is efficient and results in the production of infectious vector particles with titers comparable to that of whole retroviruses. Thus, we believe that other heterologous membrane-associated proteins can also be efficiently incorporated into the envelopes of enveloped viruses.

MoMLV is a murine retrovirus which has poor infectivity outside of mouse cells. When this ecotropic virus is adapted to produce retroviral vector particles carrying, for example, the N2 vector genome, this vector will infect only mouse cells at appreciable efficiencies. The related amphotropic N2 virus will infect cells from human, mouse and other organisms. This difference is attributable to the substitution of the amphotropic envelope protein for the ecotropic envelope protein. Both types of viral vector particles have essentially identical nucleocapsids derived from MoMLV. However, neither ecotropic N2 nor amphotropic N2 virus will infect hamster cells. As shown in the Examples provided hereinbelow, we have discovered that hamster cells can be infected by MLV[VSV G] vector particles and that addition of anti-VSV serum to preparations of these viral particles completely abolished their infectivity. Thus, we have shown that the presence of VSV G protein in the vector particles results in vectors having a host range derived from VSV, the origin of the membrane-associated protein incorporated within their envelope.

In order to determine if vector particles containing heterologous membrane-associated protein could be efficiently assembled, we tested whether the VSV G protein could be assembled with the nucleocapsid of MoMLV. We first introduced the neomycin phosphotranferase gene (Neo) which provides neomycin resistance, as a selectable marker for the vector particles into the amphotropic packaging cell line PA317. The resultant vector particles were added to cells incapable of supporting amphotropic MLV infection. Baby Hamster Kidney (BHK) cells lack amphotropic cell surface receptors and are, therefore, not susceptible to infection with amphotropic MLV-based retroviruses, as shown below in the experiments of Example 1.

In initial experiments, we confirmed that this cell line is indeed refractory to infection by amphotropic MLV retrovirus. The next set of initial experiments is shown in Example 1. In these experiments, we confirmed that amphotropic N2 virus containing the Neo gene will grow in rat 208F fibroblasts, but not in BHK cells.

EXAMPLE 1

Growth of N2 Virus in Rat 208F Fibroblasts

Amphotropic N2 virus containing the Neo gene inserted between the long terminal repeats (LTRs) of MoMLV was prepared from the producer cell line PA317/N2 and titered both on BHK cells and rat 208F fibroblasts, a cell line that is susceptible to MoMLV retrovirus infection. We observed a $10^5$-fold decrease in Neo-resistant (Neo$^r$) colony forming units (CFU) in BHK cells compared with that in rat 208F cells; thus, the BHK cell we used failed to support infection by N2 virus containing the amphotropic retroviral envelope protein.

With the initial studies completed, we produced enveloped vector particles containing heterologous membrane-associated proteins. As an example of such production, Example 2 is provided to show the production of amphotropic N2 MLV[VSV G] vector particles using an MLV-based retroviral vector encoding the VSV G protein. We assayed the MLV[VSV G] vector particles on BHK cells to determine if the host range of these vector particles had been altered relative to amphotropic MLV.

EXAMPLE 2

Generation of MLV[VSV G] Vector Particles

To produce MLV[VSV G] vector particles, we used MoMLV-based retroviral vectors as illustrated in FIG. 1, which is not drawn to scale. In pLRNL, the Neo$^r$ gene expressed from the Rous Sarcoma Virus (RSV) promoter was inserted between the LTRs of MoMLV. The MoMLV-based retroviral vector pLRNL contains the Neo-resistance (Neo) gene under control of the promoter of RSV. This vector is described in Li et al., *Virology* 171:331–341 (1989), the disclosure of which is hereby incorporated by reference. A single BamH1 site is immediately upstream of the RSV promoter. Into this BamH1 site, a 1.7-kilobase pair (kb) BamH1 fragment containing the entire coding region of VSV G gene was inserted, giving rise to the construct pLGRNL (ATCC No. 75473). This VSV G gene is described in Rose et al., *Cell* 30:753–762 (1982) and Rose et al., *J. Virol.*, 39:519–528 (1981), the disclosures of which are hereby incorporated by reference. The plasmid pSAM, also shown in FIG. 1, containing the gag region of MoMLV, a hybrid pol region between MoMLV and amphotropic virus 4070A and the env region of 4070A has been described in Miller et al., *Science*, 225:630–632, the disclosure of which is hereby incorporated by reference.

HPRT-deficient 208F cells were derived from Fischer rat cells by selection in 6-thioguanine, as described in Quade, K. *Virology*, 98:461–465 (1979), the disclosure of which is hereby incorporated by reference. Thymidine kinase (Tk)-deficient BHK cells were derived from BHK21 cells by selection with 5-bromodeoxyuridine, as described in Littlefield et al., *Nature* 211:250–252 (1966), the disclosure of which is hereby incorporated by reference. These BHK cells and 208F fibroblasts were grown in Dulbecco-modified Eagle medium (DME) with high glucose supplemented with 10% fetal calf serum (FCS).

To generate infectious vector particles, either pLGRNL or pLRNL was co-transfected into BHK cells with the helper vector pSAM expressing MoMLV gag protein, a polymerase gene and amphotropic envelope protein from the SV40 early promoter. Supernatants from transfected BHK cells were collected at 48 hours post-transfection and used to infect susceptible 208F cells and resistant BHK cells. To titer virus, cells were infected overnight with filtered supernatants in the presence of 4 mg/ml polybrene. Infected cells were selected in medium containing 400 mg/ml G418 and colonies were scored about 14 days after infection. The results of the experiment of this example are shown in Table 1.

TABLE 1

Transient vector particle production from BHK cells following cotransfection by pSAM with either pLRNL or pLGNRL

| Vector Particle | Cell infected | Titer (CFU/ml) |
|---|---|---|
| LRNL | 208F | 480 |
|  | BHK | <10 |
| LGRNL | 208F | 380 |
|  | BHK | 260 |

It can be seen from Table 1 that vector particles derived from pLRNL lacking VSV G protein were able to infect 208F cells efficiently but failed to infect BHK cells. In contrast, vector particles derived from pLGRNL, containing the VSV G protein, could infect not only 208F cells, but also BHK cells, as indicated by the appearance of Neo$^r$ colonies. Thus, the host range of the MLV[VSV G] vector particles had been altered relative to amphotropic MLV.

Accordingly, we believe that the VSV G protein produced by the pLGRNL-transfected BHK cells of Example 2 was incorporated into at least some of the retroviral vector particles, producing MLV[VSV G] vector particles capable of infecting hamster cells. Since the only VSV protein encoded by pLGRNL is the VSV G protein, the results of Example 2 shown in Table 1 also indicate that G protein alone, without the participation of other VSV-encoded proteins, is sufficient for the formation of MLV[VSV G] vector particles. Accordingly, Example 2 shows that infectious vector particles could be assembled having nucleocapsid from one virus and a heterologous membrane-associated protein.

As stated above in the background of the invention, mixed infection of VSV and retroviruses resulted in a lower titer of vector particles than what is obtained from VSV infection alone. Rather than being the result of inefficient incorporation into virions caused by poor specificity between the G protein and the retroviral nucleocapsid, we believe that this lower titer is due to the progressive inhibition of cellular protein synthesis, including those proteins encoded by the retroviruses, as a result of VSV G protein toxicity.

Thus, in order to determine whether the presence of membrane-associated protein from the same family of viruses as the origin of the nucleocapsid is necessary for the formation of vector particles, we conducted experiments to form MLV[VSV G] vector particles without any envelope protein having an origin from the same family as MLV. An example of such an experiment is shown in Example 3.

EXAMPLE 3

Formation of MLV[VSV G] Vector Particles without Env Gene Product

For this experiment, we produced two additional vectors shown in FIG. 1, pLARNL and pSVGP. pLARNL is produced from pLRNL in a manner similar to the production of pLGRNL, however, a 2.7-kb XbaI fragment containing the envelope (env) gene of amphotropic retrovirus 4070A was inserted into the BamH1 site in pLRNL. pSVGP was constructed by inserting a 5.8 kb HindIII-ScaI fragment containing the SV40 early promoter and the gag and the pol regions from pSAM into the mammalian expression vector pcD, described in Okayama et al., *Mol. Cell. Biol.*, 3:280–289 (1983), the disclosure of which is hereby incorporated by reference. "Poly A" in FIG. 1 indicates the polyadenylation signal derived from SV40.

In this example, we co-transfected pLRNL, pLARNL or pLGRNL with pSVGP into BHK cells. To generate vector particles, 10 μg of the vector DNA together with 10 μg pSVGP were co-transfected into cells by using the calcium phosphate precipitation procedure of Graham et al, *Virology* 52:456–457, the disclosure of which is hereby incorporated by reference. Culture medium was collected 36 h after transfection and filtered through a 0.45-mm filter.

The construct pSVGP contains gag and pol genes expressed from the SV40 early promoter, but the MoMLV Env gene is absent. The vector particles expressing the Neo$^r$ marker (pLARNL or pLGRNL) were titered separately on 208F and BHK cells, as described above. The titers obtained are shown in Table 2.

TABLE 2

Transient vector particle production from BHK cells following cotransfection by pSVGP with pLRNL, pLARNL or pLGRNL

| Experiment No. | Vector Particle | Cell infected | Titer (CFU/ml) |
|---|---|---|---|
| 1 | LRNL | 208F | <10 |
|  |  | BHK | <10 |
|  | LARNL | 208F | 280 |
|  |  | BHK | <10 |
|  | LGRNL | 208F | 440 |
|  |  | BHK | 680 |
| 2 | LRNL | 208F | <10 |
|  |  | BHK | <10 |
|  | LARNL | 208F | 260 |
|  |  | BHK | <10 |
|  | LGRNL | 208F | 480 |
|  |  | BHK | 720 |

It can be seen from the results of Table 2 that no infectious vector particles were detected from pLRNL and pSVGP co-transfected cells since the MoMLV env gene was absent in both plasmids. 208F cells co-transfected with pLARNL, containing the amphotropic MLV Env gene, and pSVGP produced a Neo$^r$ titer of 200–300 CFU/ml, but this preparation failed to infect BHK cells. However, both 208F and BHK cells were infected with similar efficiencies by pLGRNL derived vector particles, containing the VSV G gene, cotransfected with pSVGP. Since the LGRNL vector particles were generated in the complete absence of MoMLV env protein, the results of Example 3 shown in Table 2 lead us to the conclusion that a heterologous membrane-associated protein can be assembled into the vector particles without the participation of any envelope protein having an origin from the same family of viruses as the origin of the nucleocapsid. Since G protein is also the sole VSV-encoded protein used in this Example, this confirms that no VSV gene products other than G protein are required for the formation MLV[VSV G] vector particles. Thus, we believe that no additional gene products are generally necessary for the introduction of foreign membrane-associated proteins into vector particles.

We obtained similar titers of Neo-resistance when transiently generated LGRNL and LARNL vector particles were assayed on 208F cells. Since expression of both the retrovirus env gene and the VSV G gene is regulated by the same MoMLV LTR in these constructs, we believe the amounts of transiently produced proteins in the transfected BHK cells are similar. However, we can not exclude the possibility that the stability of the two proteins may be different. In any event, we believe that other membrane-associated proteins can be similarly expressed using these and similar constructs.

Thus, we believe that the interaction between nucleocapsids and the heterologous membrane-associated protein can be at least as efficient or more efficient than with heterologous membrane-associated protein. In the case of MLV[VSV G] vector particles, we observed greater efficiency of infection of 208F cells by MLV[VSV G] vector particles at lower titers than with vector particles having both nucleocapsid and membrane-associated protein derived from MLV. The receptors for murine retroviruses, such as MLV, have been shown to be cell surface proteins, whereas there is some evidence that a membrane phospholipid is the receptor for VSV, possibly accounting for the wide host range of VSV. Therefore, we believe that our observed Neo$^r$ titers of MLV[VSV G] vector particles reflects increased cellular susceptibility to infection with MLV[VSV G] vector particles than with env-containing MoMLV vector particles.

To ascertain if the specificity of infection with vector particles, such as MLV[VSV G], is determined by the membrane-associated protein, the vector particles can be treated with neutralizing antiserum having specificity to the membrane-associated protein. If the specificity is determined by the membrane-associated protein, such neutralizing antiserum would prevent infection by the neutralized particles. Thus, we performed the experiment of Example 4 in order to determine if vector particles having a heterologous membrane-associated protein provided a specificity of infection determined by the membrane-associated protein. In Example 4, anti-VSV serum was used to neutralize the infectivity of the MLV[VSV G] vector particles.

EXAMPLE 4

Neutralization of MLV[VSV G] Vector Particles

Vector particles, generated transiently by co-transfection of pLARNL or pLGRNL with pSVGP, were incubated at 37° C. for 45 min either with normal rabbit serum or with various dilutions (1:500, 1:100 and 1:20) of rabbit anti-VSV serum purchased from Lee Biomolecular Research Laboratories, Inc. Supernatants were harvested 48 h after cotransfection of pSVGP with pLARNL or pLGRNL into BHK cells. The vector particles were quantitated by assaying for the formation of Neo$^r$ colonies on 208F cells and BHK cells, as described above. The results are shown in Table 3.

TABLE 3

Neutralization of MLV[VSV G] vector particles with anti-VSV antibody

| Vector | Normal rabbit | Anti-VSV serum 1:500 | Anti-VSV serum 1:100 | Anti-VSV serum 1:20 | Titer (CFU/ml) in 208F | Titer (CFU/ml) in BHK |
|---|---|---|---|---|---|---|
| LLARNL | — | — | — | — | 240 | <10 |
|  | + | — | — | — | 230 | <10 |
|  | — | — | + | — | 230 | <10 |
|  | — | — | — | + | 220 | <10 |
| LGRNL | — | — | — | — | 620 | 880 |
|  | + | — | — | — | 600 | 880 |
|  | — | + | — | — | 110 | 150 |
|  | — | — | + | — | <10 | <10 |
|  | — | — | — | + | <10 | <10 |

It can be seen from the results shown in Table 3 that anti-VSV serum at a dilution of 1:100 markedly reduced the infectivity of LGRNL vector particles on both cell types whereas the titer of LARNL on 208F cells was not affected by exposure to VSV antiserum. This observation further supports our belief that VSV G protein is assembled into the vector particles of LGRNL.

As was shown by the results of Example 3 detailed in Table 2, incorporation of VSV G protein into vector particles was efficient, since vector particles transiently generated by cotransfecting pLGRNL or pLARNL with pSVGP gave similar Neo$^r$ titers on 208F cells. We next determined whether the process of incorporating membrane-associated proteins, such as VSV G protein, into particle envelopes is equally efficient in the presence of the native particle envelope protein. This determination was done by co-transfecting pLGRNL with pSAM into BHK cells and analyzing the proportions of pure vector particles and phenotypically mixed particles by anti-VSV antibody-directed, complement-mediated lysis. These experiments are shown in Example 5.

EXAMPLE 5

Complement-Mediated Lysis of MLV[VSV G] Vector Particles

Vector particles containing cell supernatant in a final volume of 200 µl of DMB-10% FCS containing various amounts of specific antisera, complement or equivalent volumes of normal serum were heated at 37° C. for 45 minutes. The mixture was then added to culture media in the presence of 4 µg/ml polybrene. Infected cells were selected in G418-containing medium as described above. Viral supernatants were harvested 48 h after cotransfection of pSAM with pLARNL or pLGRNL into BHK cells. The supernatants were treated with either 10 µl rabbit serum or 10 µl anti-VSV serum at 1:20 dilution with or without 10 µl rabbit complement. All reactions were done in a final volume of 200 µl, heated at 37° C. for 45 min. The results are shown in Table 4.

TABLE 4

Antibody complement-mediated lysis of MLV[VSV G] vector particles

| Vector particle | Normal rabbit serum | Anti-VSV serum | Rabbit complement | Titer (CFU/ml) in 208F | BHK |
|---|---|---|---|---|---|
| LARNL | — | — | — | 480 | <10 |
|  | + | — | — | 460 | <10 |
|  | — | — | + | 410 | <10 |
|  | — | + | + | 400 | <10 |
| LGRNL | — | — | — | 380 | 260 |
|  | + | — | — | 380 | 250 |
|  | — | — | + | 320 | 230 |
|  | — | + | — | 270 | <10 |
|  | — | + | + | 90 | <10 |

It can be seen from Table 4 that without any treatment, transiently generated LGRNL vector particles gave a Neo$^r$ titer of 380 CFU/ml on 208F cells and 260 CFU/ml on BHK cells. Addition of normal rabbit serum to the same vector particle preparation had no effect on titer. In contrast, the titer dropped to 270 CFU/ml on 208F cells and to background levels on BHK cells when the vector particles were pre-treated with a 1:20 dilution of the anti-VSV antibody. This result indicates a titer of LGRNL vector particles containing only VSV G protein in this preparation of approximately 110 CFU/ml on 208F cells. To determine the fraction of vector particles containing only the retroviral envelope protein and the fraction of vector particles containing both the retroviral envelope protein and the VSV G protein in this preparation, we treated the vector particle preparation with a combination of rabbit complement and the anti-VSV antibody.

The potentiating effect of complement-mediated lysis has been shown previously by others to eliminate MLV[VSV G] vector particles efficiently. Addition of rabbit complement alone to the vector particle preparation slightly reduced the Neo$^r$ titer to 320 CFU/ml on 208F cells and 230 CFU/ml on BHK cells (see Table 4), probably due to the non-specific interaction of fetal calf serum in the media with rabbit complement. Vector particles pre-treated with a 1:20 dilution of the anti-VSV antibody together with rabbit complement gave a Neo$^r$ titer of 90 CFU/ml on 208F cells. Thus, we believe that this non-neutralized population of Neo$^r$ vector particles contains only the retroviral envelope protein. This interpretation is consistent with the results also shown in Table 4, in which similar treatments of LARNL vector particles containing only retroviral envelope protein have little effect on its Neo$^r$ titer when measured on 208F cells. Thus, it is likely that VSV G protein and other membrane-associated proteins can be efficiently incorporated into vector particles even in the presence of native envelope proteins.

Retroviral DNA integrates into host chromosomes in a fashion that maintains the linear organization of the viral genome in sequences called proviral sequences. To establish that cell clones resulting from infection with enveloped vector particles having a heterologous membrane-associated protein contained proviral sequences that maintain the linear organization of the vector particle nucleic acid, we performed Southern blot analysis of LGRNL-infected clones. These experiments are shown in Example 6.

EXAMPLE 6

Southern Blot Analysis of LGRNL Infected Cells

Genomic DNA was prepared as described by Maniatis et al., "Molecular Cloning, A Laboratory Manual," Cold Spring Harbor Laboratory, Cold Spring Harbor, N.Y. (1982), the disclosure of which is hereby incorporated by reference. DNA samples were digested with appropriate restriction enzymes, electrophoresed on 0.8% agarose gels and transferred to nylon membranes. A $^{32}$P-labeled DNA probe containing the complete neomycin phosphotransferase gene prepared by priming with random deoxy hexanucleotides (Amersham) was used as a hybridization probe with the filters. Filters were washed with 0.1×SSC-0.5% SDS at 53° C. several times and subjected to autoradiography.

Figure 2:
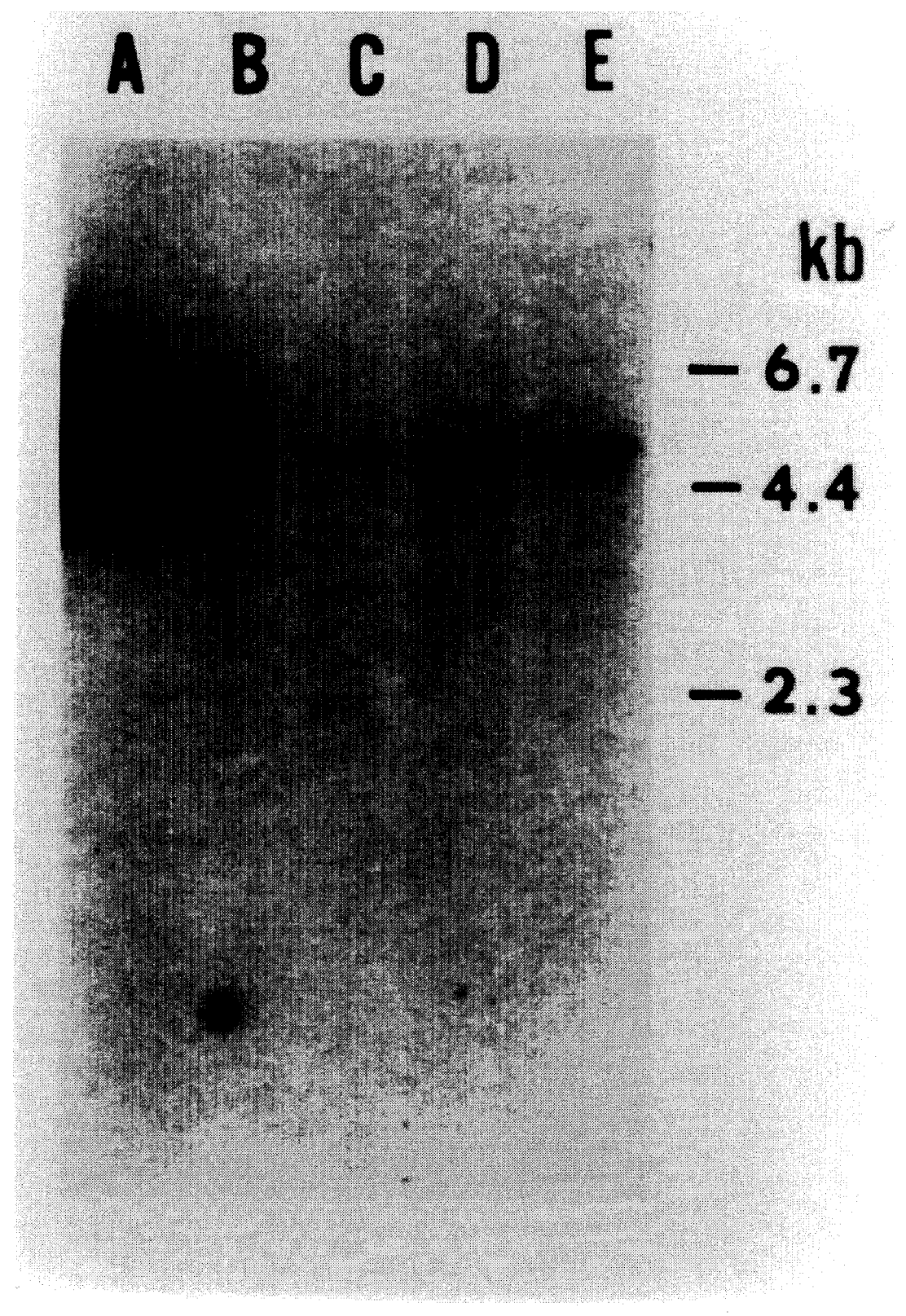

Genomic DNA was isolated from two different Neo$^r$ clones (lanes B and C) and two different Neo$^r$ BHK clones (lanes D and E) that were infected with LGRNL vector particles. DNA (10 µg) was cut with Sst1, run on a 1% agarose gel, transferred to a nylon-type filter and probed with a Neo gene-specific probe. Five nanograms of pLGRNL plasmid DNA digested with Sst1 was loaded in lane A to serve as a marker. The resulting Southern blot is shown in FIG. 2.

Sst I cleaves only once in each LTR of LGRNL and is therefore expected to yield a 5-kb fragment (see FIG. 1). As seen in lanes B through E of FIG. 2, when the chromosomal DNA from the two BHK clones and two 208F clones was cleaved with Sst I and hybridized to a probe containing the Neo gene, a fragment of about 5 kb was detected. The size of this fragment was identical to that of the Sst I-cleaved pLGRNL plasmid DNA seen in lane A. Thus, the results of Example 6 show that the LGRNL proviral DNA appears to have an uninterrupted and un-rearranged organization in the infected cells. This result is the same as that seen for wild-type retroviral infection. Thus, we believe that other recombinant vector particles will similarly form uninterrupted and un-rearranged proviral DNA sequences.

In order to illustrate that such recombinant vector particles obtain the host range of the membrane-associated protein present in their envelope, we infected a variety of cell lines with vector particles derived from pLGRNL and pLARNL. These studies are shown in Example 7.

EXAMPLE 7

Determination of Host Range of MLV[VSV G]

HeLa cells were obtained from the American Type Culture Collection. LNSV cells were derived from SV40-transformed HPRT-deficient Lesch-Nyhan cells (described in Jolly et al., Mol. Cell. Biol., 6:1141–1147 (1986), the disclosure of which is hereby incorporated by reference). Rat 208F cells and BHK cells were as previously described. Supernatants were harvested 48 h after cotransfection of pSVGP with pLARNL or pLGRNL into BHK cells. Equal volumes of each supernatant was then applied to the four different cell types and Neo$^r$ titers were determined two weeks after G418 selection. The experiment has been repeated three times and the result of one such experiment is shown in Table 5.

TABLE 5

Relative susceptibility of different cell lines to MLV[VSV G] vector particles

| Infected cell | Titer (CFU/ml)$^a$ of LARNL | LGRNL |
|---|---|---|
| 208F (rat fibroblast) | 250 | 450 |
| BHK (hamster kidney) | <10 | 680 |

TABLE 5-continued

Relative susceptibility of different
cell lines to MLV[VSV G] vector particles

| Infected cell | Titer (CFU/ml)[a] of | |
|---|---|---|
| | LARNL | LGRNL |
| LNSV (human fibroblast) | 16 | 180 |
| Hela (human carcinoma) | 12 | 30 |

As described above, the retroviral env gene of LARNL used in this study is derived from the env regions of amphotropic virus 4070A. The envelope glycoprotein encoded by this gene can bind to cell surface receptors present on cells from a wide range of mammalian species, including human cells. However, several human lines were relatively refractory to amphotropic viral infection compared to murine cells. As shown in Table 5, the Neo[r] titers of LARNL in human lines such as HeLa cells or LNSV fibroblasts are about 20 fold lower relative to that in rat 208F cells. As also shown in Table 5, LGRNL vector particles infected HeLa cells with an efficiency slightly greater than LARNL vector particles; however, they infected LNSV fibroblasts much more efficiently than did LARNL vector particles.

Due to the excellent efficiency of infection of the MLV [VSV G] vector particles derived from pLGRNL on LNSV cells, we believe that the major block to infection of LNSV cells with retrovirus is due to inefficient interaction of cell surface receptors with retroviral envelope protein. The inclusion within the retrovirus of membrane associated protein known to interact with cell surface receptors appears to overcome this block. Thus, we believe that we have discovered a general method for altering the host range of enveloped vector particles by including a heterologous membrane-associated protein within the envelope of vector particles derived therefrom.

We do not believe the relatively less efficient results seen with infection of HeLa cells by the MLV[VSV G] vector particles of LGRNL are due to poor interaction with the HeLa cell surface receptors. Rather, since VSV infects HeLa cells efficiently, we believe the less efficient results observed above are probably due to post-penetration events.

Currently, retroviral vectors provide the most efficient method for introducing new genetic information into mammalian cells. Since vector particles containing amphotropic envelope protein can infect human cells, they represent a potentially useful tool for the treatment of genetic disorders in human. However, as shown in Table 5, some human cells can be relatively resistant to amphotropic retrovirus infection. The presence of relatively few amphotropic retrovirus receptors, inefficient reverse transcription in the cytoplasm or accelerated degradation of unintegrated viral DNA in human cells can each account for the inefficient infection of human cells by the retroviral vectors.

Our discovery provides a method of increasing the efficiency of retroviral infection of human and other cells beyond the limited range provided by membrane-associated proteins derived from the same family of viruses. This discovery is that incorporating membrane-associated proteins into the retrovirus can overcome at least some of the potential blocks for infection by altering the host range of the retroviral vectors, thus facilitating more efficient transfer of foreign genes into these cells. This system uses helper virus to create an infective unit. This unit contains elements of a retrovirus that permit integration into the host genome, regulatory elements to control expression of a foreign gene, a selectable cell marker and/or other foreign genes. This unit is designed to target a given group of cells. The breadth of infectivity being defined by the ability of the engineered protein to bind a range of cell types. These component genes can be introduced into the resulting vectors through any manner known to those of skill in the art.

It is envisioned that other viruses could be used in this system. Long terminal repeats from other retroviruses could be used from a group consisting of but not limited to RSV, HIV, Avian Leukemia Virus and other murine leukemia viruses. The capsid protein could also be derived from these or other viruses.

The inventors have used in their model, an RSV promoter to control neomycin-resistance expression. Other markers include hygromycin-resistance and dihydrofolate reductase (methotrexate resistance). Similarly, other promoters could be used, including but not necessarily limited to the cytomegalovirus immediate early promoter, SV40. Promoters could be chosen so as to potently drive expression or to produce relatively weak expression, as desired.

Additionally, foreign genes for expression within a targeted cell population can be added to the vector, as will be described in more detail hereinbelow. Promoters with given tissue specificities could also be used in order to restrict expression of such foreign genes to a given cell type. For example, a pancreatic elastase promotor is specific for expression in pancreatic tissue. Another example would be the internal promoter of the human hepatitis B core gene which regulates gene expression in a liver-specific manner. Other tissue-specific promoters exist for brain and other tissues.

Membrane-associated proteins other than VSV G protein which are good candidates for providing altered host range when used in accordance with the present invention as described in the examples for VSV G protein include those proteins from other enveloped viruses that bind host receptors and facilitate infection. Our discovery allows for selective removal of any membrane-associated protein and use of this protein to create a nucleic acid delivery system that targets an altered range of cells. As one example, the gD gene from HSV (Herpes Simplex Virus) could be used in order to obtain a host range including the neural ganglia of human tissue. A large number of such viral and non-viral examples will be readily apparent to those of skill in the art.

Non-viral membrane-associated proteins could also be used to alter the host range of vector particles. We believe that proteins which interact as a ligand to a given cell receptor or cell surface moiety is a candidate to target a vector particle to a host range of cells having the given cell receptor or cell surface moiety. A suitable protein would contain binding regions which would serve to identify a host range for the vector particle. Depending on the ubiquity of the receptor for the protein in question, one could either target the viral vector to a vast range of human cells, to a subset of cells or to a single cell type. Thus, for example one could potentially target all human cells, all white blood cells, or only T-helper cells.

In one embodiment of this invention, such proteins are derived from viruses known to infect specific cell types. However, the present invention is not limited to the use of virally derived proteins. It is envisioned that any ligand/receptor duo could be exploited in this system. The requirements for an operable system being the identification of a ligand/receptor duo or, for therapy, at least an understanding of the breadth of cell types that could interact with the ligand. The utility of the system will depend on the availability of a receptor for a ligand and the affinity of a given receptor for that ligand.

In a preferred form of this invention, the membrane associated protein is a viral protein that determines a host range, such as the VSV G protein. However, virtually any protein having cytoplasmic, transmembrane and extracellular domains can be used as the membrane-associated protein. Thus, for example, CD4, known to interact with HIV gp120 on the surface of HIV infected cells, is a candidate to be used in a recombinant vector particle to deliver a foreign gene to those cells. Young et al. showed that the human CD4 cell surface protein can be assembled into retroviral particles using other techniques. The incorporation of CD4 protein into avian leukosis virus was tested by transiently expressing this protein by means of SV40-based expression vectors in quail cells previously infected with a replication-competent ALV vector. CD4 was found to be incorporated into ALV particles produced by the transfected cells. (See Young et al., Science, 250:1421–1423 (1990), the disclosure of which is hereby incorporated by reference). Other membrane-proteins of immune cells can also be introduced. The known affinities of various membrane-associated proteins can be used to define the host range of the resulting retroviral particles.

Example 8 is provided to illustrate the production of a vector which will target cells infected with HIV. The T-helper cell membrane-associated surface antigen, CD4 is known to be the major HIV cell surface receptor. The CD4 antigen has a ligand-receptor interaction with the HIV-produced protein, gp120. Thus, vector particles having CD4 associated with their viral envelope should target cells infected with HIV.

EXAMPLE 8

Vector Particle for Targeted HIV Therapy

Sequences encoding CD4 are first obtained from a T-cell line. Briefly, cells are grown in culture and lysed. Total RNA is purified from these cells using a cesium chloride gradient. The total RNA is washed and precipitated, and cDNA is synthesized therefrom using reverse transcriptase and oligo-dT primers. The resulting cDNA/RNA hybrids are used as template for Polymerase Chain Reaction (PCR) using appropriate primer pairs for CD4 that are complementary to both the 5' and 3' ends of the CD4 sequence, and include tails coding for Bam H1 restriction endonuclease sites. The PCR product is run on an agarose gel and the fragment of the expected size (approximately 1.2 kilobases) is cut and eluted from the gel. The eluted DNA is digested with Bam H1 and a promoter is added to the 5' end of this CD4 encoding sequence. The resulting sequence is cloned into the Bam H1 site in pLRNL.

Thus, Example 8 shows the production of a vector particle having a host range defined by a naturally occurring membrane-associated protein. When the ligand to be included within the viral envelope is not a naturally occurring membrane-associated protein, it is necessary to associate the ligand with the membrane. In order to accomplish this, the gene coding for the ligand can be combined with sequences coding for a membrane-associated domain. By "naturally occurring membrane associated protein", it is meant those proteins that in their native state exist in vivo in association with lipid membrane such as that found associated with a cell membrane or on a viral envelope.

In a preferred form of the present invention, this can be accomplished by recombining the gene coding for the ligand proximate of the membrane-binding domain for VSV G protein or other virally derived envelope protein that stably assembles with a given capsid protein. Thus, proteins, such as insulin, known to interact with receptors on muscle and adipose cells, potentially provide a vehicle for obtaining infectivity of cells having the appropriate insulin receptor by including the insulin gene with the VSV G sequences coding for its membrane-associated domain, or the membrane-associated sequences from another membrane-associated protein which forms a stable vector particle.

As stated above, we believe that the major block to infection of cells with enveloped vector particles is due to inefficient interaction of cell surface receptors with viral envelope protein. Thus, the exterior domain of these proteins could be linked to a membrane or interior domain to create a functional vector particle. The ligand-receptor interaction does not appear to be involved in the interaction between protein and nucleocapsid.

Although the nucleocapsid of Semliki Forest virus contains a specific receptor for the cytoplasmic tail of the viral E2 spike glycoprotein, this mechanism is not necessarily directly applicable to other enveloped viruses. Thus, for SFV and other alphaviruses, it is likely that E2 spike glycoprotein or a similar protein is required for efficient infection. Accordingly, if SFV or other alpha virus derived vector particles are to be used within the context of the present invention, it is necessary to include those portions of the E2 spike glycoprotein important for efficient interaction with the nucleocapsid.

Retroviruses, such as Rous sarcoma virus are able to produce vector particles using mutant forms of the envelope protein that lack a cytoplasmic tail. Thus, we believe that if an interaction between the envelope protein of retrovirus and its nucleocapsid is required to mediate the incorporation of the glycoprotein into the envelope of budding viral particles, such interaction occurs within or close to the lipid bilayer. Presumably, the interaction occurs within the hydrophobic membrane-associated domain of the envelope protein. Thus, we believe that for many systems, if any portion of the membrane-associated protein is important for vector particle assembly, this portion occurs within the membrane-associated domain or close to that domain.

Accordingly, we believe that forming recombinant proteins with membrane-associating domains from proteins having the ability to direct packaging, such as the VSV G protein, and at least the receptor binding portions of other ligands, whether membrane-associated or not, will permit vector particle targeting to desired cell types.

Thus, as one embodiment of the present invention, a cassette-type system is provided in which the portion of the gene coding for the membrane-associated domain from the VSV G protein or other membrane-associated protein remains as the constant portion of the cassette vector. Into this constant region is inserted portions from a desired ligand. These two domains form a recombinant protein which will interact with the nucleocapsid to provide for a structurally intact vector particle with efficient targeting capabilities for a desired cell type or types. It is important to maintain the reading frame for translation when inserting ligands into this cassette in order to obtain a full length, bifunctional recombinant protein chimera. A "protein chimera" is used to describe a product produced recombinantly by genetically linking regions of nucleic acid sequences from two or more proteins such that the encoded product, though one continuous protein, contains domains duplicating sequences of amino acids from those proteins. Consequently there is no need for using full length envelope protein or non-membrane bound protein, as long as sufficient ligand receptor interactions remain.

Thus, the present invention provides nucleic acid having functional sequences from a first virus and also sequences encoding a ligand identifying the host range of the vector particles containing the nucleic acid. By "functional" it is meant any sequences which are involved with typical wild-type replication or infection by that virus. Sequences other than those associated with typical wild-type replication or infection can also be included within the functional nucleic acids provided herein.

The nucleic acid can direct production of vector particle by itself, or can require co-transfection with a helper virus, as described above in connection with the use of LGRNL with pSVGP. With the use of these nucleic acid sequences, vector particles can be assembled that contain these host altering membrane-associated proteins, either as hybrid recombinant proteins or as expression products of a full length gene, to target a given particle to a given cell for gene delivery.

The envelope protein from a typical retrovirus, such as MoMLV, contains three domains: an exterior receptor binding domain, a membrane-associated domain and an interior (cytoplasmic) domain. Heretofore, it was thought that the cytoplasmic domain was required to interact with nucleocapsid protein for efficient particle packaging. Example 9 shows the results from an experiment that confirms that none of the retroviral envelope protein domains are required for efficient packaging of vector particles having a retrovirally derived nucleocapsid. In the experiment of Example 9, recombinant chimeric proteins having various retroviral domains were constructed and the packaging efficiency of the resulting vector particles assayed by the ability of the constructs to introduce VSV immunoreactivity into COS cells.

EXAMPLE 9

Packaging Efficiency of Vector Particles Having Retroviral/VSV G Chimeric Membrane-Associated Protein Two chimeric membrane-associated protein gene constructs were prepared. The M2 construct contained VSV G exterior receptor binding domain fused to the membrane-associated and cytoplasmic domains of MLV envelope protein. The M9 construct contained the exterior receptor binding domain and membrane-associated domain of VSV G protein, fused to sequences encoding the cytoplasmic domain of MLV envelope protein.

The M2 and M9 constructs were introduced into each of two expression vectors. The first vector, pSVL contained an SV40 late promoter and late protein polyadenylation signal. The second vector, pFR400 contained an SV40 early promoter and an HBV polyadenylation signal. Thus, four expression constructs were produced: pSVLM2, pSVLM9, pFR4M2 and pFR4M9. These expression vectors were introduced into COS cells. Plasmids containing full length VSV G membrane-associated protein (pJM) and full length MLV envelope protein (pSVLENV) were also introduced. Indirect immunofluorescence using rabbit anti VSV G protein was used to analyze VSV G protein immunoreactivity production in these cells. Table 6 gives results from these experiments.

TABLE 6

| | Transient expression in COS cells | |
|---|---|---|
| Plasmid | Estimated Percentage Positive Cells | Intensity of fluor. |
| pJM | 44.6%, 17.9% | 1000 |
| pSVLENV | 1.2% | 10 |
| pSVLM2 | 13.3% | 50 |
| pSVLM9 | 10.6% | 60 |
| pFR4M2 | 5.5% | 15 |
| pFR4M9 | 3.6% | 15 |

Full length VSV G proteins from pJM were visible both within the cell and on the cell surface. Hybrid M9 proteins were only visible in perinuclear regions. By fluorescent activated cell sorting (FACS) it was determined that only 10% of these cells expressed hybrid M9 protein on their cell surface. The molecular weight of the hybrid proteins were confirmed by immunoprecipitation using Rabbit anti VSV G. The mobilities were consistent with the protein size predicted from the nucleotide sequences.

The results of the experiments of Example 9 indicate that the most efficient packaging resulted from full length VSV G protein, with either of the hybrid proteins with MLV cytoplasmic domains being expressed less efficiently on the cell surface. As discussed above, this finding was unexpected due to the prevailing belief that retroviral cytoplasmic domain was required for efficient vector particle packaging of vector particles having retrovirally derived nucleocapsid. Thus, Example 9 confirms our surprising discovery that enveloped vector particles having nucleocapsids derived from a particular virus can be efficiently packaged with heterologous membrane-associated proteins.

Example 9 also indicates that the VSV G protein cytoplasmic and membrane domains are efficient at directing protein to the cell surface. Thus, it is believed that hybrid protein could be created in a manner similar to the manner of Example 9, wherein the cytoplasmic and membrane domains of VSV G protein are combined to create a cassette for vector particle targeting where exterior receptor domains from a variety of unrelated proteins could be used with the cassette.

As stated above, we believe that the regions of membrane-associated proteins involved with vector particle formation lie chiefly within the membrane-associated domains of the protein. Thus, recombinant chimeric membrane-associated proteins useful in the vector particles of the present invention contain the membrane-associated domain from a membrane-associated protein shown to be efficiently packaged into vector particles. The exterior receptor domains of these chimeric proteins can be selected from any ligand/receptor to determine a host range, as described above. Example 10 is provided as one example of the production of vector particles having a recombinant chimeric membrane-associated protein.

EXAMPLE 10

Cassette for Production of Vector Particles Having Chimeric Membrane-Associated Protein The hybrid membrane associated glycoprotein is constructed following guidelines set forth in Example 9. As a model for this example, the VSV G cytoplasmic and membrane domains are genetically recombined with the gene encoding erythropoietin (EPO). This recombinant chimera is inserted in expression vector pSVL from Example 9. In addition, vector pLRNL and vector pSVGP are transfected into producer cells. The resulting supernatant is collected and the vector particles are used to infect B6SutA cells. B6SutA cells contain the EPO receptor and under neomycin selection, only those cells receiving vector particles containing EPO hybrid protein and pLRNL vector particle genome will survive.

The methodology described in Example 10 can be used to create a cassette system in which genes for any desired receptor binding domain can be recombined with the membrane-associated domain from VSV G protein or other membrane-associated domain. Thus, Example 10 provides methods for the rapid production of a variety of vector particles having a host range defined by the receptor binding domain inserted into the cassette.

Vector particles having non-native membrane-associated ligands as described herein, will, advantageously, have a host range determined by the ligand-receptor interaction of the membrane-associated protein. For example, where the membrane associated protein is derived from an enveloped virus capable of infecting human cells, the vectors will be able to introduce foreign genes into human cells with greatly increased efficiency. The neomycin gene used in the previous examples could be substituted with a therapeutic gene that would also be under the control of the RSV promoter. Similarly the therapeutic gene could be introduced in addition to the neomycin gene. As mentioned, there are a number of promoters and marker genes that could be used in this system. Therapeutic genes could take the form of nucleic acid sequences encoding protein or nucleic acid sequences with inherent regulatory value.

Therapeutic genes encoding protein could take the form of polypeptide to supplement a given protein defect, to improve or alter an immune function or one that would render a specific protein or set of proteins inactive. The therapeutic protein could potentially have regulatory activity to stimulate or inhibit a protein or set of proteins. The therapeutic protein could also stimulate or inhibit a given cell function. In other words the therapeutic gene could encode a polypeptide with a range of activities not necessarily limited to this discussion but selectable to those individuals with skill in the art.

The nucleic acid could also code for a product having activity as nucleic acid. For example, this nucleic acid could have antisense activity to prevent translation of a given protein or it could have DNA binding capabilities that could promote or inhibit expression of protein or a set of proteins or promote or inhibit a given cell function. Again, the sequence of choice would be apparent to an individual with skill in the art.

Thus, for targeted gene therapy, a vector particle having altered host range can be produced using the methods of the present invention. The ligand will be selected to provide a host range including the targeted cell type. Thus, in order to provide therapy for a genetic defect in which a polypeptide is not expressed in sufficient quantities or in sufficient quantities of active form, the ligand will be selected so as to target the cell types that normally produce that polypeptide. The gene for the polypeptide should also be introduced under the control of an appropriate viral promoter.

Alternatively, therapy can also be provided by inhibiting the expression of undesired polypeptides, e.g. through the production of anti-sense oligonucleotides which interfere with the translation of mRNA coding for the undesired polypeptides. Example 11 is provided to illustrate the production of a targeted vector particle delivering a therapeutic oligo-nucleotide for HIV infection.

EXAMPLE 11

Delivery Vehicle for Anti-HIV Therapeutic Agent

The vector particle from Example 8 is altered by replacing the Neo gene with a sequence encoding an antisense oligonucleotide for a region complementary to the mRNA of the major HIV protease. The resulting vector particles contain CD4 as a membrane-associated protein and direct the transcription of antisense mRNA that hybridizes with HIV mRNA to restrict HIV replication.

Thus, Example 10 shows a technique wherein a vector particle genome is modified to direct a particular therapy to particular cell types. It is also contemplated that the present invention include the targeting of progenitor cells. For example, there are a number of progenitor cell types found in bone marrow that differentiate into blood cells. Many blood cells have relatively short life spans and therefore progenitor cells continually divide and differentiate to replace the lost cells. Therapies directed to blood cells would be most useful if they target the progenitor cell. These cells are known to have unique cellular determinants that permit histological identification and could be used as cell receptors for the membrane-associated proteins of the vector particles of the present invention. The vectors could be constructed to target these cell types for gene delivery by including an expressible gene which encodes a membrane-associated protein that binds to a unique cellular determinant of such progenitor cell types. Examples of such progenitor cell types which could be targeted using vector particles of the present invention include pluripotent stem cells, erythroblasts, lymphoblasts, myeloblasts and megakaryocytes.

It is further envisioned that the therapy of the present invention be performed either in vivo or in vitro. For in vitro therapy of an organism, cells could be removed and infected with the vector particle in vitro. For vector particles having membrane-associated proteins which determine the appropriate host range, there would be no need to purify the cells to be targeted in vitro because the viral vector would specifically infect the appropriate cells. Thus, bone marrow samples could be removed from a subject and the desired cell type transfected. These transfected cells could then be returned to the organism of origin of the cells or, where rejection of the cells is not envisioned to be a problem, to another organism. The sample could be treated with growth factors in vitro either before or after transfection to increase the number of cells to be either targeted or returned to the subject organism.

In order to further the goals of altering the host range of these viral vectors, we have discovered that the development of stable packaging cell lines constitutively expressing membrane-associated proteins would facilitate even further the generation of retroviral vectors with wider host range and with increased efficiency of infection in human and other cells. Many of these membrane-associated proteins, including the VSV G envelope protein, are toxic to cells. This results in producer line stability problems because expressor cells die quickly, resulting in difficulties in creating more than transient production. Although some cell types (e.g., human 293, its derivative 2–3 which makes gag and pol proteins from MLV, or hamster BHK cells) will grow after transduction with vector particle LGRNL and neo selection, this growth lasts only four weeks and then the cells die. Other cell types die even more rapidly. Thus, the development of stable packaging cell lines is highly desirable.

One method for producing stable packaging cell lines is to develop a packaging construct in which the envelope protein is subject to an inducible promoter in which expression of the envelope protein can be turned on or off through the presence or absence of a particular compound or through a change in conditions such as temperature. One example of such an inducible promoter is the mouse mammary tumor virus (MMTV) promoter. The MMTV promoter is highly inducible by corticosteroid and their analogues in cells which synthesize glucocorticoid receptor proteins in sufficient amounts.

A cell line having the ability to express vector particle genes from an inducible promoter, such as the MMTV promoter, will not produce vector particle without induction by appropriate inducing conditions, e.g. the presence of corticosteroid for the MMTV promoter. Accordingly, a cell line having the ability to produce vector particles can be stably maintained without the production of vector particles. A subpopulation from the cell line could then be induced to produce vector particles by the appropriate conditions when desired. An example of the production of a stable packaging cell line having the ability to express vector particle genes under the control of an inducible promoter is shown in Example 12.

EXAMPLE 12

Production of Stable Packaging Construct with Inducible Promoter

In order to identify a cell line which synthesize glucocorticoid receptor proteins in sufficient amounts to provide for induction of the MMTV promoter in the presence of corticosteroid, a construct with the MMTV promoter directing transcription of a marker gene such as the chloramphenicol acetyl transference (CAT) gene is produced. This construct is introduced into various cell lines, with or without dexamethasone treatment.

Those cell lines exhibiting a ratio of CAT activity in the dexamethasone treated cells to that in the untreated cells greater than 25:1 are preferred for use as stable packaging cell lines under the control of the inducible MMTV promoter. A cell line exhibiting such a ratio is the BHK cell line.

To produce a stable packaging cell line for MLV[VSV G], BHK cells are permanently transfected with a packaging construct, pSVGP and subsequently with a construct linking the MMTV promoter to the VSV G gene and to RSV LTR driving the hygromycin resistance gene, as a selectable marker. Hygromycin-resistant cells are selected and checked for Gag and Pol production by Western blots using anti-MLV 30 as probe. These cells are also checked for the presence of the MMTV-VSV G gene by a Southern blot analysis.

Cells that continue to grow (and hence make non-lethal levels of VSV-G) are tested by transient transfection with a vector such as LRNL, treated or not treated with dexamethasone and the ratio of neo resistant colony forming units determined. The cell clones with the best performance are permanently transfected with MLV[VSV G] vector particle producing nucleic acid. Infectious particle production is induced for short periods of time (1–3 days) by dexamethasone treatment.

Thus, Example 12 shows one example of the production of a stable packaging construct under the control of an inducible promoter. Similar techniques can be used to produce a variety of vector particles of the present invention under the control of MMTV promoter or other inducible promoters.

Another example of the production of a stable packaging construct involves the development of cells which can tolerate the production of the membrane-associated protein. One cell line, MDCK, (ATCC No. CCL[34]) has been reported to be resistant to the toxic effects of VSV and to be capable of supporting long-term production of VSV-G. Other such cell lines are believed to exist. However, not all VSV G protein produced by such cell lines is functional. Accordingly, clones producing functional protein must be selected. An example of the production of stable packaging cell line producing functional membrane-associated protein is shown in Example 13.

EXAMPLE 13

Production of Stable Packaging Construct in Tolerated Cell Line

MDCK cells were tested for their tolerance to the stable expression of VSV G membrane associated protein and for their ability to produce vector particles. VSV G tolerance was tested by infecting MDCK cells with MLV[VSV G] vector particles and selecting for G418 resistant clones. The vector particles were produced from the transient transfection of pLGRNL into human 293 cells that stably expressed the retroviral gag and pol proteins. The vector particle-containing supernatant of these transfected cells was used to infect MDCK cells. These vector particles contain pLGRNL as their vector genome and VSV G as their membrane-associated protein.

MDCK cells were infected and the cells were cultured for 24 hours prior to selection in G418. At 24 hours post-infection, the cells were treated with 400 µg/ml of the neomycin analog G418. After about 7–10 days of selection, colonies began to appear that were resistant to G418. When the colonies were clearly visible and separated from non-resistant cells, they were pooled and subcultured in the presence of G418 for further analysis.

The above-described polyclonal cell line was tested for the expression of VSV G from the pLGRNL vector genome. Briefly, the cells were grown to 60–70% confluency and incubated in methionine-free medium without fetal calf serum (Met⁻ DME) for 30 minutes at 37° C. The medium was replaced with 2 mls of Met⁻ DME containing 300 µCi of $^{35}$S-methionine and incubated for an additional 4 hours. Cells were washed with ice cold PBS and 1 ml of RIPA lysis buffer (150 mM NaCl, 1% NP-40, 0.5% deoxycholate, 0.19% SDS, 50 mM Tris pH 8.0) containing 10 µl of the protease inhibitor, PMSF, at a concentration of 1 mM was added to each plate. The plates were incubated on ice for 15–30 minutes, followed by a 10 minute centrifugation after transfer of the lysed cell material to a microfuge tube. The supernatant was removed and either stored at −70° C. or used directly for immunoprecipitation. These lysates were prepared for immunoprecipitations by first treating with non-immune rabbit serum to pre-clear non-specific binding activity.

Immunoprecipitations were performed by incubating a volume containing 1×10$^7$ counts of pre-cleared lysate with about 5 µl of rabbit anti-VSV G antibody overnight at 4° C.

Protein A-Sepharose (100 µl of a 10% solution in RIPA buffer) was then added, followed by incubation for 1–2 hours at 4° C. The conjugates were washed three times in RIPA buffer and the final pellets were resuspended in 30 µl of Laemmli sample buffer. Immunoprecipitates were separated by SDS-PAGE and visualized by fluorography. The results are shown in FIG. 3. Lanes 1 and 2 show the polyclonal cell line immunoprecipitated with anti-VSV G and normal rabbit serum, respectively. Lane 3 is mock infected MDCK cells immunoprecipitated with anti-VSV G antibody. The band migrating at $M_r$ of approximately 68 kD corresponds to the VSV G protein and documents that these MDCK cells support the long term expression of VSV G.

The MDCK/VSV G polyclonal cell line was also tested for its ability to generate VSV G-containing vector particles. To do this, the cells were co-transfected with pTKhygro as a selectable marker and pSVGP to supply the gag/pol functions.

The polycation Polybrene (Aldrich, Milwaukee, Wis.) was used for the co-transfection of MDCK/VSV G cells. Briefly, exponentially growing cells were harvested by trypsinization and replated at $5 \times 10^5$ cells per 100 mm dish in 10 mls of medium containing 10% FCS. Cultures were incubated for 18–20 hours at 37° C. in an atmosphere of 10% $CO_2$. Transfection DNA (2 µg of pTKhygro and 18 µg of pSVGp) was mixed with 3 mls of serum-containing medium followed by the addition of 30 µg of Polybrene. This transfection solution was applied to the cells after removal of the medium. Cells were incubated for 10 hours. The DNA medium mixture was aspirated and mixed with 2 ml of a DMSO solution (3 parts DMSO:1 part medium). The cells were incubated for 5 minutes at room temperature. After 3 washes with medium, the cells were incubated for an additional 48 hours in complete medium. At this time, the cells were incubated in selective medium containing hygromycin (400 µg/ml) and G418 allowing for the selection of doubly-resistant cells. Hygromycin-resistant and G418-resistant colonies were pooled as described previously and VSV G-containing vector particle production was titered on BHK cells.

Infection of BHK cells with vector particles derived from the resistant cells yielded about 100–200 G418-resistant colonies per 10 ml of media. This result demonstrated that the MDCK polyclonal cell line could generate functional vector particles containing the VSV-G envelope glycoprotein and the pLGRNL vector genome.

Figure 4:
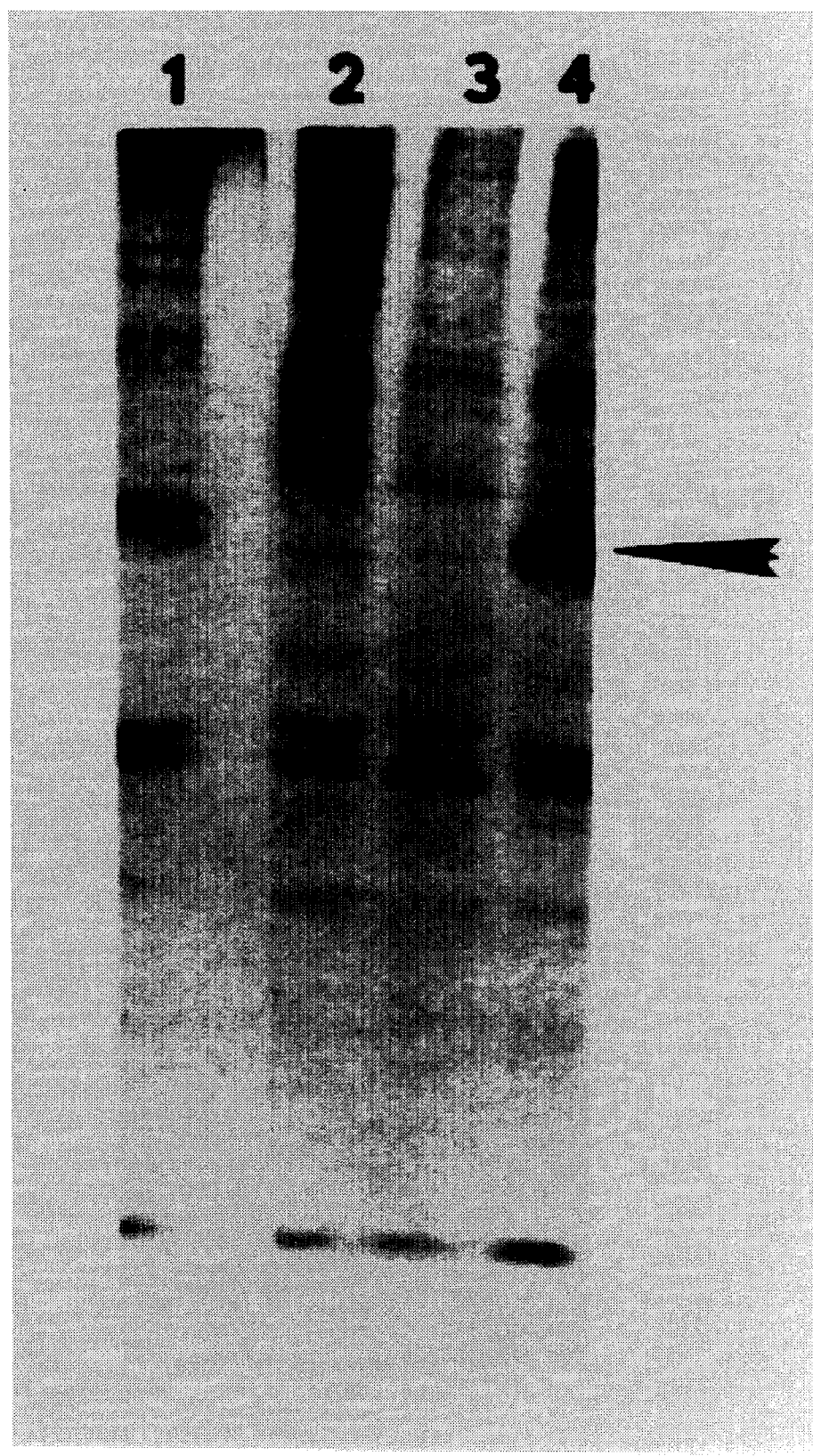
FIG. 4 shows immunoprecipitates of selected cells pooled, grown for 1 week, and then reisolated by FACS sorting. Lane 1 shows the extracts of the twice-sorted cells immunoprecipitated with the anti-VSV-G antibody and lanes 2, 3 and 4 correspond to lanes 3, 2 and 1 of FIG. 3, respectively.

A stable packaging cell line that does not contain a packaging-competent vector particle genome but does stably express VSV-G, gag and pol was then constructed in a two-step transfection procedure. In the first step, pTKhygro and pSVG (VSV G under the control of the SV40 early promoter) were co-transfected using Polybrene into MDCK cells and selected for hydromycin resistance as described previously. The resistant cells were pooled and the cells co-expressing VSV G were isolated by fluorescent activated cell sorting (FACS). Briefly, subconfluent plates were washed once in PBS and then treated for 15 minutes at 37° C. with 10 mM EDTA to remove cells from the dish. The cells were transferred to a 15 ml centrifuge tube, pelletted by low speed centrifugation, resuspended in DME plus 2% FCS and re-centrifuged. Media was removed and the pellet was resuspended in 0.5 mls of a 1:200 dilution of normal rabbit serum or a 1:200 dilution of rabbit anti-VSV G antibody. Cells were incubated with the antibody for 30 minutes on ice and then diluted with 5.0 mls of DME plus 2% FCS, followed by low speed centrifugation. The resultant pellets were washed an additional two times with 5 mls of DME plus 2% FCS. The cell pellet was resuspended in a 500 µl PBS solution containing the secondary antibody and incubated on ice for 30 minutes. Following the incubation period, the cells were washed as described above and the final pellet was resuspended in 0.5 ml of DME plus 2% FCS with Pen/Strep and Fungizone and injected into the cell sorter. Selected cells were pooled, grown for 1 week, and then reisolated by FACS sorting. These twice-sorted cells were analyzed for VSV G expression by immunoprecipitation with anti-VSV G antibody as described previously. The results are shown in FIG. 4 where lane 1 shows the extracts of the twice-sorted cells immunoprecipitated with the anti-VSV-G antibody and lanes 2, 3 and 4 correspond to lanes 3, 2 and 1 of FIG. 3, respectively. These results demonstrate that the pSVG transfected cells stably express substantial levels of VSV G.

The second step in producing the stable packaging line was to co-transfect pSVGP and a plasmid that expresses dihydrofolate reductase (DHFR) to achieve the stable expression of the gag and pol genes. DHFR was used for the selection of stable transfectants when grown in the presence of methotrexate (MTX). The plasmids were co-transfected as described previously using Polybrene and replated at 48 hours post transfection in the presence of 5 µM MTX. MTX-resistant colonies are pooled and tested for the generation of vector particles by transient transfection of these cells with a packaging competent vector genome. Supernatants are collected at 48 hours and the production of infectious vector is titered on target BHK cells as described previously.

Thus, Example 13 shows the production of a permanent VSV G packaging line by selective screening for functional VSV G protein production in cell lines resistant to the toxic effect of VSV G protein. As will be readily apparent to those of ordinary skill in the art, similar methods can be used to create cell lines which produce functional membrane-associated protein from a variety of sources.

We have shown that the VSV-G protein can substitute completely for the MoMLV envelope protein in retrovirus particles whose infectivity is destroyed by exposure to anti-VSV-G neutralizing antibodies. While demonstrating unequivocally that VSV-G protein can fully replace the MoMLV envelope protein, the method described above transiently produced only very low titers ($10^3$ cfu/ml) of LGRNL (VSV-G) virus.

To improve vector production, we have made attempts at construction of a stable packaging cell line constitutively expressing retroviral gag and pol and VSV-G protein, but heretofore such efforts have been thwarted by the toxicity of VSV-G. Example 13 describes the production of a VSV G packaging line in cell lines resistant to the toxic effect of VSV G protein. A further example of the production of a stable packaging cell line involves taking advantage of a period during which cells express sufficient VSV-G to support virus production (titers of $10^5$–$10^6$) before presumed accumulation of VSV-G at the cell surface can lead to syncytia formation and cell death. An example of improved vector production is shown in Example 14.

EXAMPLE 14

Generation of Pseudotyped Retroviral Vectors

To generate pseudotyped retroviral vector, the plasmids pLSRNL and pLGRNL were used. Either the VSV-G gene (G) or the hepatitis B surface antigen gene (S) is expressed from the murine sarcoma virus (MSV) LTR (5'L). The gene for neomycin phosphotransferase (N) is expressed from the RSV promoter (R).

To generate producer cells, the human Ad-5-transformed embryonal kidney cell line 293 (ATCC CRL #1573) was co-transfected at a ratio of 10:1 with pCMV gag-pol which encodes the MoMLV gag and pol genes under the control of the CMV promoter and pFR400 which encodes an altered dihydrofolate reductase with reduced affinity for methotrexate (Simonsen et al., *Proc. Natl. Acad. Sci.*, 80:2495–2499 (1983)). Transfected cells were selected in methotrexate ($5\times10^{-7}$M) and dipyridimole ($5\times10^{-6}$ M). Colonies were screened for extracellular reverse transcriptase activity (Goff et al., *J. Virol.*, 38:239–248 (1981)) and intracellular $p30^{gag}$ expression by Western blotting with goat anti-p30 antibody (NCI antiserum #77S000087). A clone was chosen which expressed the retroviral genes stably without the need for continued methotrexate selection.

To produce LGRNL (VSV-G) and LSRNL virus, 20 µg of plasmid DNA was transfected into either 293 cells containing the gag and pol genes but lacking an envelope gene, or PA317 cells (ATCC #CRL 9078) containing MoMLV gag, pol, and retroviral env genes. Cells were exposed to G418 (400 µg/ml; Geneticin, Sigma, St. Louis, Mo.) 48 hrs. after transfection. Supernatant from confluent cultures of G418-resistant producer cells was filtered (0.45 µm) and viral titers were determined.

Virus titers were determined by infection of Madin-Darby canine kidney cells (MDCK) (ATCC #CCL-34) in the presence of 4–8 µg/ml polybrene (Sigma). MDCK cells were chosen because these polarized epithelial cells are relatively resistant to the fusogenic properties of VSV-G protein expressed on the cell surface and can therefore form stable colonies after infection with VSV-G-containing vectors. To determine viral titers, we exposed MDCK cells to G418 12–24 hrs. after infection with virus and counted the resistant colonies after 10–12 days in selection.

To demonstrate the presence of immunoreactive VSV-G on the surface of pLGRNL-transfected 293-gag-pol cells, we performed FACS analysis of live cells stained with a monoclonal antibody to VSV-G. The anti-VSV-G antibody was an $IgG_{2a}$ antibody I1. Other appropriate anti-VSV-G antibodies can be produced using monoclonal antibody generation techniques well known in the art. Briefly, confluent monolayers of 293-LGRNL cells were incubated at 37° C. with 10 mM EDTA to remove live cells from the plate. Cells were suspended in DMEM with 2% FCS, centrifuged at 500×g at room temperature, and resuspended and incubated sequentially with the following reagents: (a) 3% normal goat serum in phosphate buffered saline (pH 7.4)×20 min. at room temperature, (b) anti-VSV-G monoclonal antibody (I1 hybridoma supernatant, undiluted) or purified mouse immunoglobulin (1 µg/ml, Cappel, Durham, N.C.)×30 min. at 4° C., and (c) FITC-conjugated goat F(Ab')2 fragment to mouse immunoglobulins (Cappel) diluted 1:40 in DMEM with 2% FCS×30 min. at 4° C. Cells were washed once between each incubation with DMEM with 2% FCS. Cells were counterstained with propidium iodide and 5,000 live cells were analyzed by flow cytometry on an Ortho Cytofluorograph 50-H. Cells stained with monoclonal antibody were compared to the negative control cells stained with control mouse immunoglobulin.

Figure 5:
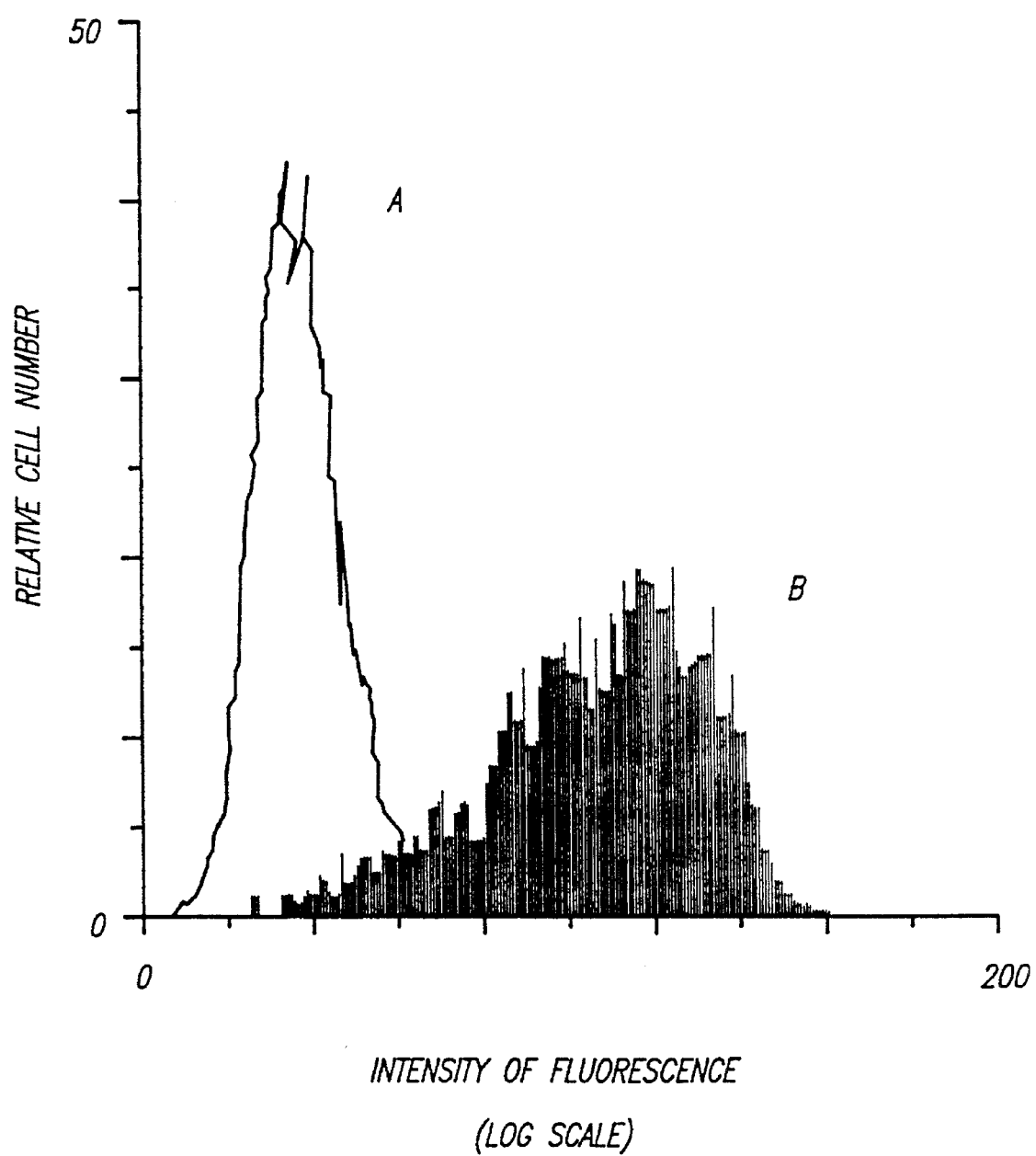
FIG. 5 depicts the flow cytometric analysis of VSV-G protein expression on the surface of 293 producer cells stably transfected with the MoMLV gag and pol genes. The results for both negative control cells stained with mouse immunoglobulin (A) and cells stained with anti-VSV-G monoclonal antibody (B) are shown.

On Day 9 after selection in G418, 90.9% of cells expressed VSV-G on their surface (FIG. 5). Sequential collection and titration of viral supernatants demonstrated that virus production was maximal during the second week after G418 selection (data not shown). Syncytia formation and subsequent cell death was first observed in the third week after selection and progressed to involve the entire monolayer. Titers of virus determined on MDCK cells as described above ranged from $5\times10^5$ to $4\times10^6$ cfu/ml.

While stable expression of low levels of VSV-G have been reported in candidate producer cell lines such as mouse C127 cells (Florikiewicz et al., *J. Cell Biol.* 97:1381–1388 (1983) and MDCK cells (Roman et al., *Exp. Cell Res.*, 175:376–387 (1988), cell surface expression of VSV-G was insufficient to support efficient retroviral vector production.

With the method of Example 14, we have taken advantage of a period during which cells can express sufficient VSV-G to support virus production of titers of $10^5$–$10^6$ cfu/ml before accumulation of VSV-G at the cell surface can lead to syncytia formation and cell death.

Electrostatic interaction at the cell surface plays an important role in vital attachment and cell entry (Conti et al., *Res. Virol.*, 142:17–24 (1991); Toyoshima et al., *Virology*, 38:414–426 (1969)). In order to overcome electrostatic repulsion between vectors and host cells, and thereby further increase the level of vector production, we examined the effect of different concentrations of polycations on the efficiency of infection of MDCK cells. We tested the following polycations: polybrene, protamine sulfate, and poly-L-lysine These experiments are shown below in Example 15.

EXAMPLE 15

Effect of Polycations on Virus Titer

To determine the effect of different concentrations of polycations on virus titer, we compared poly-L-lysine (0.25–25 µg/ml, Sigma), protamine sulfate (1.25–250 µg/ml, Sigma), and polybrene (2.5–80 µg/ml, Sigma) added to the medium just prior to infection of MDCK cells with virus.

For both vectors, optimum efficiency of infection measured by the number of G418-resistant cells occurred in the presence of 8 µg/ml of polybrene. Substitution of protamine sulfate (1.25–5.0 µg/ml), a drug approved for human use and for human gene therapy model studies, resulted in a 2 or 4-fold decrease in infection efficiency for LSRNL and LGRNL (VSV-G), respectively. Similarly, infection in the presence of poly-L-lysine (2.5–10.0 µg/ml) resulted in a 2-fold decrease in infection efficiency for both vectors. Complete omission of polycation resulted in a 100-fold reduction in the number of infected cells. Thus, Example 15 shows that polycations can significantly increase the level of viral production.

To verify that LGRNL was replication-competent on its own, we looked for replication-competent helper virus contaminating our LGRNL (VSV-G) viral stocks. We examined viral supernatants for the ability to rescue LSRNL from cells containing integrated provirus. The testing is described below in Example 16.

EXAMPLE 16

Examination of Viral Stocks for Helper Virus

To examine our viral stocks for the presence of replication-competent helper virus, we infected 293 cells containing one copy of LSRNL provirus (293-LSRNL cells) with either LGRNL (VSV-G) or replication-competent MA virus (Miller et al., *Mol. Cell Biol.* 5:431–437 (1985)). Briefly, stably infected MDCK-LSRNL cells were infected in the presence of polybrene (4 μg/ml) with either 2×10$^5$ cfu/ml of LGRNL virus stock or 2 ml of replication-competent MoMLV-derived MA virus culture supernatant. Culture supernatants were harvested after one week and the presence of rescued LSRNL was determined by exposure of 208F cells to culture supernatants followed by isolation of infected cells by G418 selection. Cultures were maintained in G418 for one week after superinfection. The culture supernatant was replaced with DMEM, incubated overnight, filtered (0.45 μm), and 1 and 10 ml aliquots used to infect to mouse 208F cells to determine virus titer.

No evidence of LSRNL rescue was observed with LGRNL (VSV-G) viral stocks. In contrast, LSRNL was efficiently rescued by MA virus from the 293-LSRNL cells (data not shown). Thus, Example 16 demonstrates that LGRNL growth did not appear to be the result of a trans-acting helper virus.

While retroviral infection usually requires interaction between the viral envelope protein and specific cell surface receptor proteins, VSV-G interacts with a phospholipid component of the cell membrane to mediate viral entry by membrane fusion. Since viral entry seems not be dependent on the presence of specific protein receptors, VSV has an extremely broad host cell range. We further tested the ability of the substitution of VSV-G for the MoMLV envelope protein to confer upon the pseudotyped particle the desirable property of increased host cell range. Determination of the host cell range of the modified retroviral vector of the present invention is described in Example 17.

EXAMPLE 17

Determination of Host Cell Range

To examine the host cell range of the modified retroviral vector, we infected BHK, zebrafish, chum salmon, and rainbow trout cell lines with the two retroviral vectors, LGRNL (VSV-G) and LSRNL produced from PA317 cells (mouse fibroblast cell line expressing MoMLV gag, pol, and env proteins).

ZF4 cells are a stable polyploid cell line derived from dissociated whole zebrafish embryos (Driever et al., In vitro Cell Develop. (in press)). ZF4 cells were maintained at room temperature in 25 $cm^2$ flasks with 5% $CO^2$ in medium containing DMEM/F12 (50/50) with 2 mM glutamine, 10% fetal calf serum, 100 U/ml penicillin, and 100 μg/ml streptomycin. RTG-2 cells (ATCC #CC1-55), derived from rainbow trout gonad, and CHSE-214 (ATCC #CRL 1681), derived from chum salmon embryo, were maintained in flasks as for the ZF4 cells in Eagle's MEM with Earle's basic salt solution and non-essential amino acids supplemented with additives as for the ZF4 cells.

The efficiency of LGRNL(VSV-G) and LSRNL infection of the different cells is shown below in Table 7.

TABLE 7

Efficiency of LGRNL(VSV-G) and LSRNL infection of different cells

| | Virus titer (cfu/ml) | |
|---|---|---|
| Cell line* | LSRNL | LGRNL(VSV-G) |
| MDCK | $1.5 \times 10^6$ | $4.6 \times 10^5$ |
| BHK | $<2.0 \times 10^2$ | $1.8 \times 10^5$ |
| ZF4 | $<2.0 \times 10^2$ | $3.0 \times 10^3$ |
| RTG-2 | $<2.0 \times 10^2$ | $1.0 \times 10^3$ |
| CHSE-214 | $<2.0 \times 10^2$ | $5.2 \times 10^4$ |

*Key to cell lines: MDCK = Madin Darby canine kidney, BHK = baby hamster kidney, ZF4 = zebrafish, RTG-2 = rainbow trout gonad, CHSE = chum salmon embryo.

No G418-resistant colonies were detected in multiple experiments in the fish cell lines infected with LSRNL virus containing the MoMLV envelope protein. In contrast, infection with LGRNL (VSV-G) reproducibly yielded G418-resistant colonies. The efficiency of infection was reduced 10–460-fold compared to infection of MDCK cells with the same virus. Unexpectedly, all fish cell lines infected with LGRNL (VSV-G) proliferated in culture in the presence of 800 μg/ml G418 with no apparent cytotoxicity. In many mammalian cell lines infected with LGRNL, we observed syncytia formation and cell death due to VSV G cytotoxicity.

We evaluated one explanation for the unexpected lack of cytotoxicity in fish cell lines by conducting FACS analysis. We evaluated whether infected fish cells have immunoreactive VSV-G on the cell surface by the FACS analysis described above. Unexpectedly, we found that no immunoreactive VSV-G protein was detected in this analysis. While not wishing to be bound to any particular explanation for the unexpected ability of the VSV-G-containing vectors to infect all fish cell lines without toxic effect, we believe that the lack of cytotoxicity of VSV-G protein in fish cells is due to the fish cells' inability to express VSV-G on the cell surface. This result can be explained by the failure of faithful intracellular processing of mature VSV-G protein. This mechanism has been well-documented following VSV infection of mosquito (Schloemer et al., *J. Virol.,* 15:1029–1032 (1975)) and duck embryo cells (Levinson et al., *Virology,* 85:621–616 (1978)). However, we have not established the presence or distribution of intracellular VSV-G. An alternative explanation is that the retroviral long terminal repeat (LTR) is not functional in these cells. Regardless of the exact mechanism, the lack of VSV-G cell surface protein appears to have permitted continued growth of these fish cell lines without syncytia formation and cell death. Moreover, the G418-resistance of infected cells indicates that the neomycin phosphotransferase gene is stably expressed from the provirus.

Thus, we have shown that the modified vectors of the present invention can mediate stable gene transfer in non-mammalian species, such as fish, which cannot be infected by other retroviral vectors, including those containing the MoMLV envelope protein. The inability of vectors containing the retroviral envelope protein to infect fish cell lines is likely due to failure of these cells to express the appropriate virus receptor.

Using the modified vector particles of the present invention, stable gene transfer into fish cell lines can be effected. Ordinarily, stable gene transfer using retroviral vectors cannot occur without integration of the provirus into the cellular genome. Thus, the ability of fish cells to support viral/cell membrane fusion, virus uncoating, reverse transcription, and integration of the provirus can be inferred from the ability of LGRNL (VSV-G) to confer stable G418-resistance to these cell lines.

Heretofore, germ line transmission and stable expression of an integrated foreign gene have been difficult to achieve in fish. Although current methods for creation of transgenic fish, including microinjection and electroporation of foreign DNA into embryos, have achieved germline transmission, the integrated DNA is often transcriptionally inactive and has been found, in many cases, to be highly rearranged. Thus, these previous efforts have resulted in high levels of genetic instability. One explanation for such instability is that injected plasmid DNA is maintained as an extrachromosomal element and overreplicated in fish over extended periods of time. The use of retroviral vectors, as in the present invention, circumvents these problems through proviral integration into the cellular genome.

We have discovered that the vectors of the present invention can be used to stably transform a wide variety of non-mammalian species. In order to further demonstrate the ability of the retroviral vectors of the present invention to stably transfect a wide variety of non-mammalian species, we conducted infection experiments in mosquitos and Xenopus, as described in Examples 18–19.

To demonstrate the ability of the retroviral vector constructs of the present invention to transform cells from a mosquito cell line, the experiment described below in Example 18 was performed.

EXAMPLE 18

Integration of Vector DNA Into Mosquito Cell Line

Mosquito cells from the *Aedes albopictus* cell line C6/36 were grown in commercially available Leibowitz medium supplemented with 10% fetal calf serum and antibiotics. Cells were grown at 27° C. in 125- or 250 ml T-flasks. Untreated control cells had an average doubling time of 27 hours.

Cells were grown to 30% confluency before treatment. Polybrene was added to a final concentration of 4 µg/ml in each flask. LGRNL virus was added to the medium and the mixture was allowed to incubate for 24 hours. Control flasks consisted of untreated and mock infected cells. The neomycin analogue, G418, was added to a final concentration of 1 mg/ml and the progress of cell death was monitored. After four weeks, virus infected cells were forming foci while the control cultures were losing cells. Thus, the exogenous neo gene appeared to be expressed in LGRNL-infected cells.

Moreover, we conducted PCR using a neo primer pair to demonstrate that the infected cells actually contained the neo gene. Approximately half of the remaining cells were removed from each of the cell cultures (infected cell culture and two control cultures). DNA from each culture was subjected to PCR detection and amplification using a neo primer pair. Vector DNA was detected (positive PCR) in the virus-infected cells. A negative PCR result was obtained with cells from both control cultures. Thus, the mosquito cells infected with LGRNL stably contained the neo gene from LGRNL.

We also tested the ability of the retroviral construct of the present invention containing VSV-G to stably infect and integrate into the genome of Xenopus cells, as in Example 19.

EXAMPLE 19

Integration of Vector DNA into the Xenopus A6 Cell Line

Figure 7:
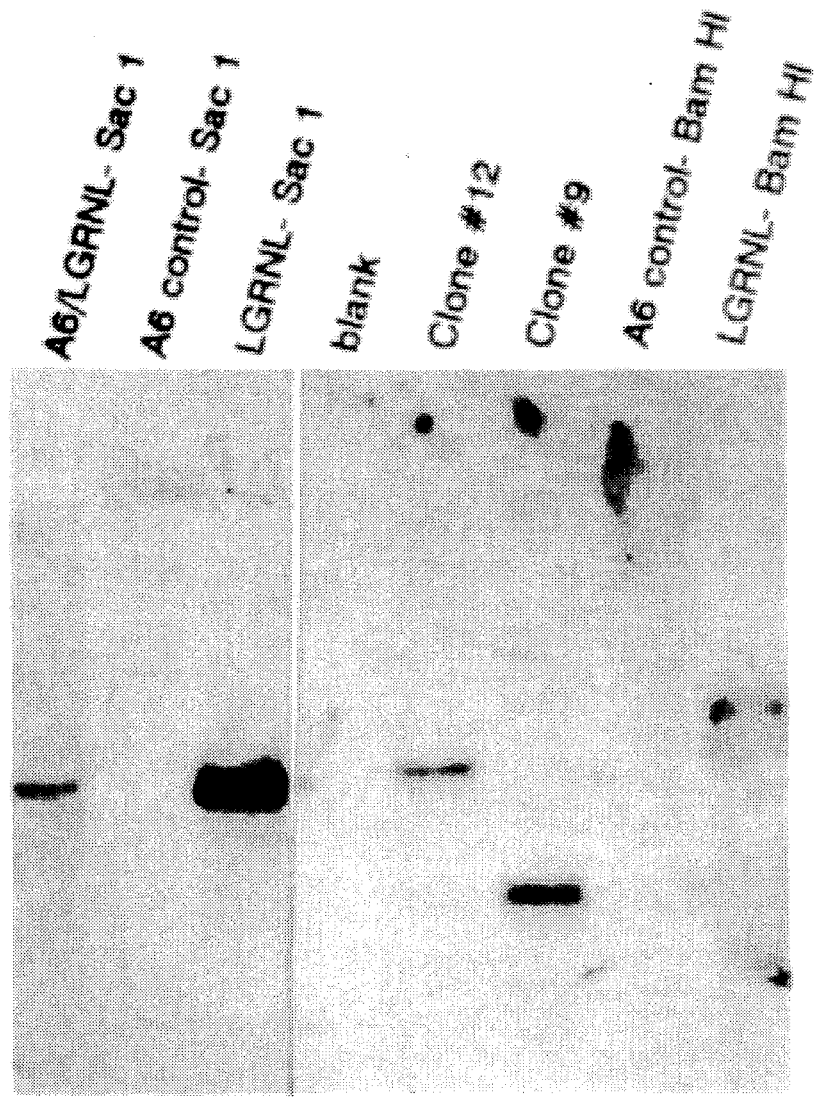
FIG. 7 shows the results of PCR of genomic DNA extracted from LGRLN(VSV-G) infected and control (non-infected) Xenopus A6 cells. Lane 1 shows the fragment from Sac I digestion of uninfected A6 cells. Lanes 2 and 3 show the fragment from Sac I digestion of plasmid pLGRNL infected cells. Lanes 5 and 6 show Bam HI digest of A6 clones. Lane 7 shows the fragment from Bam HI digestion of uninfected A6 cells, and Lane 8 shows the fragment from Bam HI digestion of plasmid pLGRNL infected cells.

Cells from the Xenopus A6 cell line were infected with LGRNL (VSV-G). To detect the presence of vector DNA in cells exposed to this vector, Southern blotting was performed. The results are shown in FIG. 7. Genomic DNA extracted from LGRNL (VSV-G) infected and control (noninfected) Xenopus A6 cells were hybridized with a neo probe. Lane 1 shows the fragment from Sac I digestion of uninfected A6 cells. Lanes 2 and 3 show the fragment from Sac I digestion of plasmid pLGRNL infected cells. Lanes 5 and 6 show Bam HI digest of A6 clones. Lane 7 shows the fragment from Bam HI digestion of uninfected A6 cells, and Lane 8 shows the fragment from Bam HI digestion of plasmid pLGRNL infected cells. It can be seen that genomic DNA in LGRNL infected contained a band that hybridized to the neo gene from LGRNL, and that control cells lacked such a band. Thus, we have shown that the DNA from the vector particles of the present invention is contained in the genomic DNA of cells from Xenopus with a single integration event per cell.

Based on the ability of the VSV-G containing retroviral particles of the present invention to infect such widely disparate non-mammalian species as fish, mosquitoes, and frogs, we have demonstrated the wide applicability of the present invention. One of ordinary skill in the art can readily adapt the foregoing techniques to infect other non-mammalian animal species, including other amphibians, insects or fish, lizards, birds and crustaceans.

We tested the ability of the vectors of the present invention to transform non-mammalian animals in vivo. An example of such in vivo transformation in zebrafish embryos is provided in Example 20.

EXAMPLE 20

Detection of Vector DNA in Zebrafish Embryos

Zebrafish embryos at the 8–64 cell stage were exposed to mild pepsin digestion and decorticated, followed by exposure to supernatant containing either the LSRNL or LGRNL(VSV-G) vector in the presence of 4 µg/ml Polybrene for 7 hours at 28° C. Among the embryos exposed to viral supernatant after the midblastula transition, the survival rate was 60–70% at 30 hours post-infection, compared to a survival rate of 70–90% in mock infected embryos. Only 1–10% of the embryos survived exposure to the viral supernatant at an earlier stage than the midblastula transition. Infected embryos were then harvested, and whole embryo nucleic acid extracts from batches of 10 embryos were prepared for PCR analysis. The extracts were incubated in 100 µl lysis buffer (10 mM Tris pH 8.4, 50 mM KCl, 1.5 mM $MgCl_2$, 0.3% Tween 20, and 0.4% NP40) at 98° C. for 10 minutes, followed by overnight incubation at 55° C. in the presence of 1 mg/ml Proteinase K. Embryo lysates were phenol extracted, the aqueous fraction ethanol precipitated, and the resulting pellet air dried and resuspended in 60 µl $H_2O$.

The equivalent of one embryo, 1/10th of the extract from 10 embryos, was used as the template for PCR analysis of integrated viral DNA. Gene amplification was performed in a volume of 20 µl in the extraction buffer with 0.2–0.5 µM oligonucleotide primers, 200 µM each dNTP, and 1–2 U Taq DNA polymerase (Perkin-Elmer, Norwalk, Conn.). The oligonucleotide primers used are as follows: neo gene primers, SEQ ID NO.1, SEQ ID NO.2; Hepatitis B surface antigen primers; and VSV-G primers: SEQ ID NO.3, SEQ ID NO.4. Thermal cycling conditions were 94° C.×1 minute, 62° C. (58° C. for HBsAg)×1 minute, 72° C.×1 minute, for 40 cycles with a final extension step at 72° C.×5 minutes. Half of the PCR product was resolved on a 2% agarose gel, transferred to a nylon membrane, hybridized with a $^{32}$P-random primer-labelled 349 bp neo PCR product from pLGRNL, or a 1.665 kb gel-purified, BamH1 digest of pLGRNL, or a 473 bp HBsAg PCR product from pLSRNL, and exposed to film for 10 hours.

Figure 6:
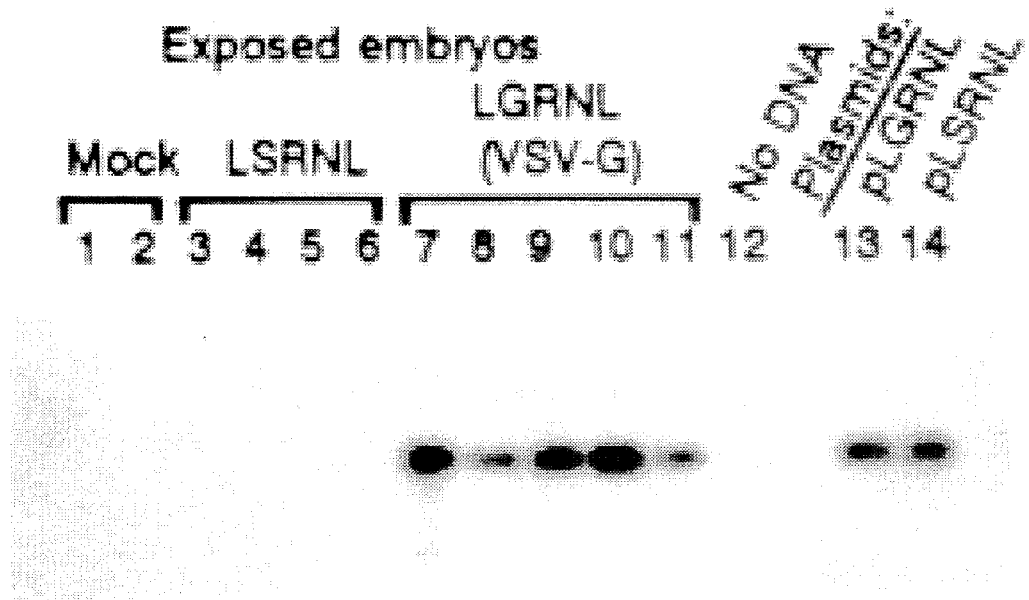
FIG. 6 shows the hybridization (using a $^{32}$P-labelled neo PCR product probe) of amplified DNA extracted from 40 wild type embryos (Lanes 1–2), 40 LSRNL-exposed embryos (Lanes 3–6), 50 LGRNL(VSV-G)-exposed embryos (Lanes 7–11), the no DNA negative control (Lane 12), 100 pg pLGRNL (Lane 13) and 0.1 pg pLSRNL (Lane 14).

FIG. 6 shows the hybridization (using a $^{32}$P-labelled neo PCR product probe) of amplified DNA extracted from 40 wild type embryos (Lanes 1–2), 40 LSRNL-exposed embryos (Lanes 3–6), 50 LGRNL(VSV-G)-exposed embryos (Lanes 7–11), the no DNA negative control (Lane 12), 100 pg pLGRNL (Lane 13) and 0.1 pg pLSRNL (Lane 14). It can be seen that LGRNL infected embryos reliably contained the neo gene from the vector, and that control embryos lacked this gene. Thus, we have demonstrated stable introduction of exogenous genetic material into zebrafish embryos.

A significant percentage of zebrafish embryos that are treated in the manner of Example 20 are expected to contain the exogenous genetic material in their germ line. Such embryos can be grown into adult fish and bred in order to propagate a phenotype expressed by the exogenous genetic material. Genes that code for any of a variety of characteristics can be included in a vector according to the present invention. For example, a gene that encodes the rainbow trout growth hormone gene can be expressed from a rous sarcoma virus (RSV) promoter as a dicistronic construct with the neo gene. The rainbow trout growth hormone gene has been previously cloned and is readily available for this purpose. A tissue-specific promoter could also be used in order to express a gene in a particular tissue only.

Another fish gene that has been previously cloned that can be transferred to another fish species encodes an antifreeze protein. Salmon in some regions of the world are particularly sensitive to changes of a few degrees celsius, and a drop in temperature can decimate their population. Thus, the fish antifreeze protein gene can be transferred to salmon using the vector of the present invention in order to prevent these sharp declines in salmon population.

Still another possible desirable gene transfer in fish would transfer genes encoding antisense messages to pathogenic organisms, such as viruses. Alternatively, genes that encode an antigen from a pathogenic organism can be transferred in order to vaccinate fish against the pathogenic organism.

No reliable and stable transformation of mosquitos has been possible in the prior art. Although genes have been transferred to mosquitos successfully in the prior art using a variety of procedures, these procedures have not produced a high enough frequency to be reliable. Moreover, the genes transferred have either been unstable over time or undergone genetic rearrangements during incorporation.

Advantageously, the vectors of the present invention can be used to transform mosquitos stably at a high frequency. The vector can be used to transfer exogenous nucleic acids into the germ line of the mosquitos in order to effect a stable mosquito line. In order to verify that foreign DNA can be incorporated into the germ line of mosquitos, the experiment of Example 21 is performed.

EXAMPLE 21

Detection of Foreign DNA in Subsequent Mosquito Generations

Fertilized mosquito eggs are allowed to grow to the blastula stage. A micromanipulator is used to microinject a small quantity of LGRNL into blastulas. A mock injected group is also prepared. Procedures similar to those that are well described for drosophila embryos are used for microinjection. The eggs are allowed to develop into adults. These adults are allowed to breed and the eggs from each pair are stored. The adults are then sacrificed and PCR conducted using the neo primers described above in connection with the zebrafish transformation of Example 20. The eggs from adults containing the neo gene based on the PCR analysis are allowed to develop into adults and bred once again. These $F_2$ adults are then checked for the neo gene using the neo PCR procedure. Eggs from those adults having a positive neo PCR contain the neo gene in the germ line.

Thus, following the procedures of Example 21, one can obtain stable mosquito lines carrying exogenous genes in their germ line. Genes other than neo can be substituted or used in addition to neo when operatively linked to an appropriate promoter to provide expression in mosquitos. Techniques for expression in mosquitos are well known and have been used for transient expression successfully in the past. However, the use of the vector of the present invention to transform the mosquito germ line, advantageously, allows such expression to occur stably over many generations.

Many examples of possible gene transfers into mosquitos can advantageously be conducted. As one example, genes can be introduced which interfere with the normal life cycle of important parasites spread by mosquitos, such as malaria or leishmania, or other human pathogens, including dengue viruses and arboviruses.

As discussed above, germ line transmission and stable expression of an integrated foreign gene have heretofore been difficult to achieve. We have identified a monoclonal antibody having binding specificity for germ cells of zebrafish. This antibody is useful in identifying germ cells for isolation and infection with viral vectors, which results in improved germ cell infection and germ line transmission. Use of this monoclonal antibody is described in Example 22.

EXAMPLE 22

Identification of Zebrafish Germ Cells Using Monoclonal Antibody

Zebrafish embryos at the 8–64 cell stage are subjected to mild pepsin digestion, and stained with a monoclonal antibody against zebrafish germ cells. FACS analysis of the cells is performed on an Ortho Cytofluorograph 50-H. Cells stained with the monoclonal antibody are isolated and infected with LGRNL by bathing the cells in viral supernatant. The germ cells are then reimplanted in zebrafish embryos.

The embryos from Example 22 can then be grown into adults, bred and tested as described in connection with mosquitos in Example 21. The fish carrying transferred genes in their germ lines stably express exogenous genes over multiple generations. Similar techniques using an antibody for mosquito or other organism's germ cells can also be developed in order to expedite gene transfer into the germ line of other organisms using the vector of the present invention.

Another important attribute of the VSV-G pseudotyped particles in addition to their broadened host cell range is their ability to withstand the shearing forces encountered during ultracentrifugation. Although MoMLV retrovirus particles and other retroviruses can be concentrated to some extent by ultracentrifugation, the severe loss of infectivity sharply limits the usefulness of this method. Most helperfree retroviral vectors produced by packaging cell lines such as PA317 are limited to titers of $10^5$–$10^7$ cfu/ml (Miller et al., *Mol. and Cellular Biol.,* 6:2895–2902 (1986)). These titers are generally adequate for many ex vivo gene transfer applications. However, the requirement for subsequent selection and prolonged culture of transduced cells is disadvantageous and could be averted with higher vector titers that cannot be obtained using standard techniques. Moreover, for some retroviral vector-mediated gene transfer applications, especially in vivo gene therapy studies requiring infection of a large number of cells, virus preparations of higher titer are required in order to prevent an undue burden in preparation.

Another aspect of the present invention relates to the ability to obtain high titer solutions of retroviruses. There have been two types of limitations suggested for preparing very high titers of retroviruses. One limitation relates to retroviral susceptibility to shearing during concentration methods such as ultracentrifugation, filtration, chromatography or others. Another limitation relates to the tendency of highly concentrated viruses to clump or fuse with adjacent particles. We have unexpectedly discovered that the retroviral vectors of the present invention containing VSV-G membrane-associated protein can be concentrated to high titer. The experiments of Example 23 were conducted in order to verify that a so-pseudotyped vector would permit concentration of vector particles by ultracentrifugation.

EXAMPLE 23

Concentration of Virus

We harvested supernatants from confluent monolayers of 293-LGRNL and PA137-LSRNL producer cells from 10 cm tissue culture dishes after overnight incubation in 6 ml of DMEM-high glucose with additives as described above. Supernatants were filtered (0.45μ) and subjected to ultracentrifugation in a Beckman Model L3-50 centrifuge in an SW41 rotor at 40,000×g (25 k rpm) at 4° C. for 90 min. The pellet was resuspended overnight at 4° C. in 30 μl of either TNE (50 mM Tris Ph 7.8, 130 mM NaCl, 1 mM EDTA) or 0.1% Hank's balanced salt solution. To concentrate the virus further, a second cycle of ultracentrifugation was performed. Pellets from 6 tubes were resuspended in a total volume of 360 μl and were concentrated again by ultracentrifugation. Pre- and post-concentration virus titers were determined on MDCK cells as described above.

The results of the concentration of vector particles by ultracentrifugation are shown in Table 8.

cycle of ultracentrifugation, we concentrated the viral stock to $2\times10^9$ cfu/ml. In contrast, concentration of LSRNL by identical procedures produced only a 4-fold increase in LSRNL titer with less than 1% recovery of infectious particles.

Thus, we have reproducibly achieved a 100 to 300-fold concentration of the virus with a single cycle of ultracentrifugation and 94–100% recovery of infectious particles. Preferably, this method will yield a recovery of at least 50% of the cfu's present prior to centrifugation, and still more preferably over 90%, as we have demonstrated here.

To explore further the differences between the LGRNL (VSV-G) vector and LSRNL, we examined the stability of retroviral vectors under different environmental conditions. This testing is described in Example 24.

EXAMPLE 24

Temperature Stability of Retroviral Vectors

The stability of the infectious particles in DMEM with 10% FCS at 37° C., 4° C. and after multiple freeze-thaw cycles was determined. The results are shown in Table 9.

TABLE 9

Stability of retroviral vectors under different environmental conditions

| Condition | LSRNL | | LGRNL (VSV-G) | |
|---|---|---|---|---|
| | Virus Titer (cfu/ml) | % virus remaining | Virus titer (cfu/ml) | % virus remaining |
| No treatment | $2.6 \times 10^6$ | — | $1.2 \times 10^5$ | — |
| Hours at 37° C. | | | | |
| 2 | $1.7 \times 10^6$ | 65% | $7.0 \times 10^4$ | 58% |
| 4 | $1.7 \times 10^6$ | 65% | $5.0 \times 10^4$ | 42% |
| 6 | $6.2 \times 10^5$ | 24% | $4.0 \times 10^4$ | 33% |
| 8 | $3.5 \times 10^5$ | 13% | $2.0 \times 10^4$ | 17% |
| O/N at 4° C. | $<2 \times 10^3$ | <1% | $2.0 \times 10^3$ | 2% |
| Freeze/thaw cycles | | | | |
| 2 | $1.3 \times 10^6$ | 50% | $1.2 \times 10^5$ | 100% |
| 4 | $1.9 \times 10^6$ | 73% | $7.0 \times 10^4$ | 58% |
| 6 | $1.6 \times 10^6$ | 61% | $8.0 \times 10^4$ | 67% |

Incubation of both vectors at 37° C. resulted in a progressive decrease in the number of infectious particles with a resulting decrease in titer of approximately 10-fold over an

TABLE 8

Concentration of vector particles by ultracentrifugation

| Virus | No. of conc. cycles | Virus titer (cfu/ml) | | | Total virus (cfu) | | % virus recov. |
|---|---|---|---|---|---|---|---|
| | | Pre-conc. | Post-conc. | Fold conc. | Pre-conc. | Post-conc. | |
| LGRNL | 1 | $1 \times 10^6$ | $2.2 \times 10^8$ | 220.0 | $8.2 \times 10^7$ | $7.9 \times 10^7$ | 96.0 |
| | 2 | $1 \times 10^6$ | $2.0 \times 10^9$ | 2,000 | $8.2 \times 10^7$ | $6.0 \times 10^7$ | 73.2 |
| LSRNL | 2 | $2.1 \times 10^6$ | $8.0 \times 10^6$ | 3.8 | $2.8 \times 10^7$ | $2.4 \times 10^5$ | <1.0 |

The results reported above are for 82 ml of culture supernatant at a titer of $1\times10^6$ cfu/ml, concentrated by ultracentrifugation at 50,000×g. Pelleted virus resuspended in a total volume of 360 μl of 0.1×Hank×s balanced salt solution demonstrated a 220-fold increase in virus titer with 96% recovery of infectious particles. After an additional 8 hr. period. Incubation of the viral stocks in medium overnight at 4° C. resulted in a decrease in titer of approximately 100-fold. Furthermore, the vectors were equally sensitive to repeated freeze-thaw cycles with approximately 60% of infectivity remaining after 6 cycles. Thus, the difference in the envelope proteins of the two vectors did not significantly affect the temperature stability of the particles.

In conclusion, we have prepared a retroviral vector pseudotype with VSV-G which permits infection of a broad range of host cells and allows concentration of the virus to titers of greater than $10^9$ cfu/ml. This class of retroviral vector pseudotype extends the use of retroviral vectors for stable gene transfer and genetic studies in previously inaccessible species. Furthermore, the ability to make high titer virus preparations has application for in vivo gene therapy studies.

The previous Examples have shown that retroviral vectors pseudotyped with the VSV G envelope protein have a broad host range and increased efficiency of infection, and can be concentrated to high titers by means such as ultracentrifugation. However, as previously noted, retroviral production by mammalian cells expressing VSV G protein is limited, since transient or constitutive expression of the VSV G protein can cause syncytia formation and cell death in most mammalian cells.

High-titer retroviral vector production is desirable in many applications. However high-titer production is especially important in human gene therapy trials in which direct gene transfer in vivo is desired. Thus, we have developed further improved methods for generating a stable packaging cell line capable of producing retroviral vectors at relatively high titers.

We produced a stable cell line which harbors the retroviral vector of interest without envelope protein. These cell lines produce all of the components necessary for retroviral packaging except for an envelope protein. Accordingly, the cell lines include nucleic acid corresponding to the retroviral long terminal repeats (LTR's), retroviral gag and pol, and may also include a desired exogenous polynucleotide sequence. Since the cells do not express the toxic envelope protein, the cell line can be maintained indefinitely. High-titer retroviral production is initiated in this cell line by introducing into a subpopulation of cells nucleic acid encoding a functional membrane-associated protein.

In one preferred form of the invention, 293GP cells, which contain the gag and pol genes but lack any envelope gene, are used as initial host cells, into which the retroviral LTR's containing a desired exogenous gene can be introduced to generate the cell line described above. Other suitable initial host cell lines are known to those of skill in the art and can also be used. Preferably, the host cells will provide for high levels of expression of the retroviral gag and pol genes.

In an alternative embodiment, the cell line harbors the nucleic acid encoding functional membrane-associated protein in a condition where the protein is not expressed. In this embodiment, retroviral production is initiated by altering the conditions so as to express the membrane-associated protein. For example, the membrane-associated protein can be operatively linked to a temperature sensitive promoter in which essentially no production of protein occurs below a given temperature. Examples of such temperature sensitive promoters are well known by those having ordinary skill in this art. Production of protein can be initiated in the cells of this embodiment by raising the temperature to a point where protein expression can occur. A large number of promoters that are induced under a wide variety of differing conditions are also known. As will be apparent to those having ordinary skill in the art, these other promoters can also be used in connection with this embodiment of the invention.

Once an initial host cell line is formed that contains the retroviral gag and pol, a desired exogenous gene of interest is introduced using an appropriate vector. Preferably, the gene is introduced using a viral vector carrying the retroviral LTR's and the gene of interest. However, it is also possible to introduce the genes of interest into the host cells by transfection with an appropriate plasmid that also carries the LTR's and desired gene.

An example of the production of a stable cell line which harbors retroviral vector with an exogenous gene of interest but lacks the gene encoding an envelope protein is described in Example 25.

EXAMPLE 25

Production of Stable Cell Line Harboring Retroviral Vector

Figure 8:
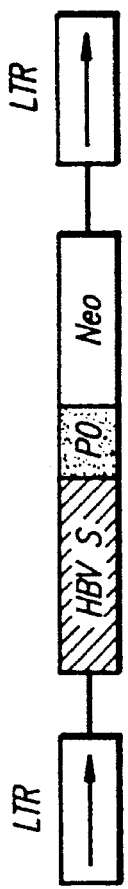
FIG. 8 shows the structure of the pLSPONL retroviral vector.

We constructed the retroviral vector pLSPONL that carries an exogenous neomycin resistance gene. The structure of pLSPONL is shown in FIG. 8.

The pLSPONL retroviral construct contains the gene encoding the surface antigen (S) of hepatitis B virus (HBV) controlled by the 5' long terminal repeat (5'LTR). A segment containing the internal ribosome entry sequence derived from the poliovirus DNA (PC) followed by the gene encoding the bacterial neomycin phosphotransferase (Neo) was inserted immediately downstream of the HBV S gene.

To generate infectious LSPONL virus, we transiently transfected 20 μg of pLSPONL in PA317 cells (ATCC #CRL-9078) which contain MoMLV gag, pol and retrovital env genes. The resulting LSPONL viruses were collected 48 hours after transfection. The LSPONL virus was then used to infect 293GP initial host cells. As described above, these initial host cells are capable of substantial expression of retroviral gag and pol.

After infection with the LSPONL virus, the 293 GP cells were exposed to media containing 400 μg/ml G418 to select those cells expressing the gene for neomycin resistance. G418-resistant colonies were picked 2 weeks later. The presence of HBsAg was determined by ELISA, and the clone that secreted the highest amount of HBsAg into the culture medium was picked and used for the subsequent production of the LSPONL virus.

Because of the absence of a gene encoding a toxic membrane-associated protein, the cells harboring the LSPONL retroviral vector described in Example 25 can be stably maintained for an indefinite period.

Infectious retroviral particle production is initiated by introducing into a subpopulation of this cell line nucleic acid that encodes a membrane-associated protein. The remaining cells are reserved without initiation of retroviral particle production for future production. The nucleic acid encoding the membrane-associated protein can be introduced by transfection of a plasmid carrying the gene operably linked to a promoter capable of driving expression in the host cells. Preferably, the promoter drives expression at a relatively high level in order to rapidly produce large quantities of retroviral particles. The membrane-associated protein gene can also be introduced using other methods known to those having ordinary skill in the art such as by infection with a viral vector carrying the gene.

An example of the production of retroviral particles using the VSV G protein as membrane-associate protein is shown in Example 26.

EXAMPLE 26

Production of Infectious Retroviral Vectors

Figure 9:
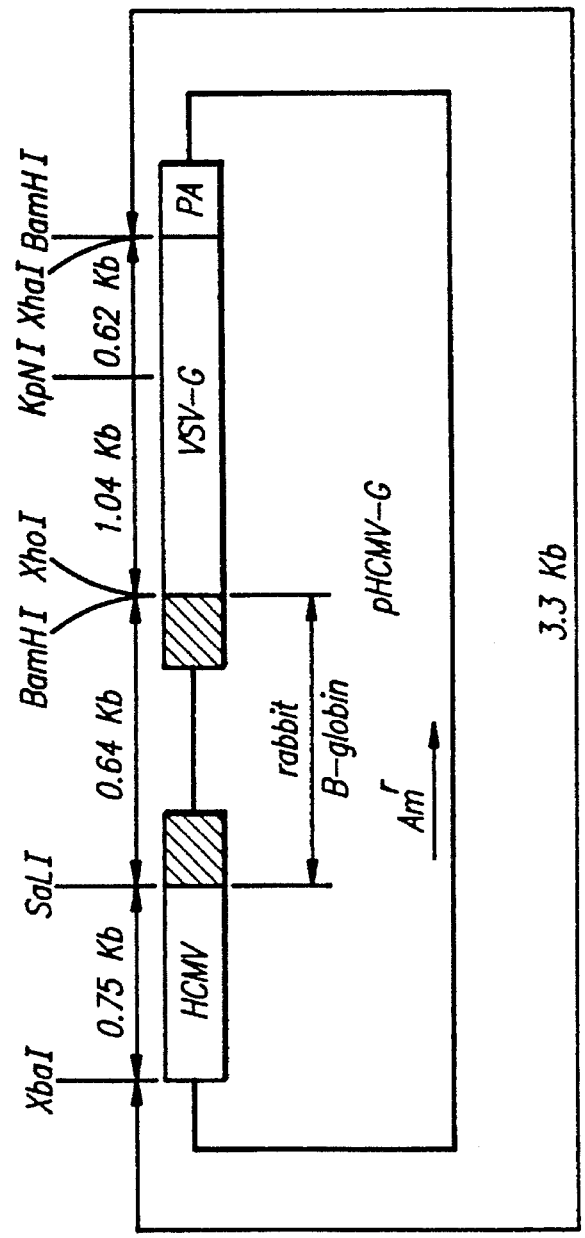
FIG. 9 is a restriction map of the pHCMV-G plasmid.

To generate the pseudotyped LSPONL virus, we transiently transfected 30 μg of pHCMV-G plasmid (ATCC Accession No. 75497) into the clone harboring the LSPONL provirus from Example 25. This plasmid contains the VSV-G gene controlled by the strong immediate early promoter derived from the human cytomegalovirus. The plasmid also contains the polyadenylation signal of the rabbit β-globulin gene and the ampicillin resistance gene of pBR322. A restriction map of this plasmid is shown in FIG. 9.

The LSPONL virus generated by the host cells transfected with pHCMV-G was collected and pooled between 48 and 96 hours after transfection. The G418-resistance titer of the pseudotyped virus LSPONL(G) relative to that of its amphotropic counterpart LSPONL(A) was determined in rat 208F fibroblast cells and also in various human cell lines including human cervical carcinoma line (HeLa), human tracheal epithelium line (9HTEO), human foreskin fibroblast line (Basinger), human skin fibroblast line (TO-119), and human glioblastoma lines U251, U-138, Hs683, U373MG and LNA-E8. The amphotropic vector LSPON L(A) was made by the traditional methods of retroviral vector production through the use of PA317 producer cells. These traditional methods of retroviral vector production are well known to those having ordinary skill in the art.

The results are shown in FIG. 10. It can be seen that the G418 resistance titer was higher for the LSPONL(G) virus infected cells in 8 of the 10 cell lines tested.

Thus, the results of the experiment of Example 26 demonstrate that the VSV-G pseudotyped virus can infect human cells more efficiently than its amphotropic counterpart. To confirm these results, we determined the infection efficiency of LSPONL(G), as described in Example 27.

EXAMPLE 27

Infection Efficiency of the LSPONL(G) Virus

Figure 11:
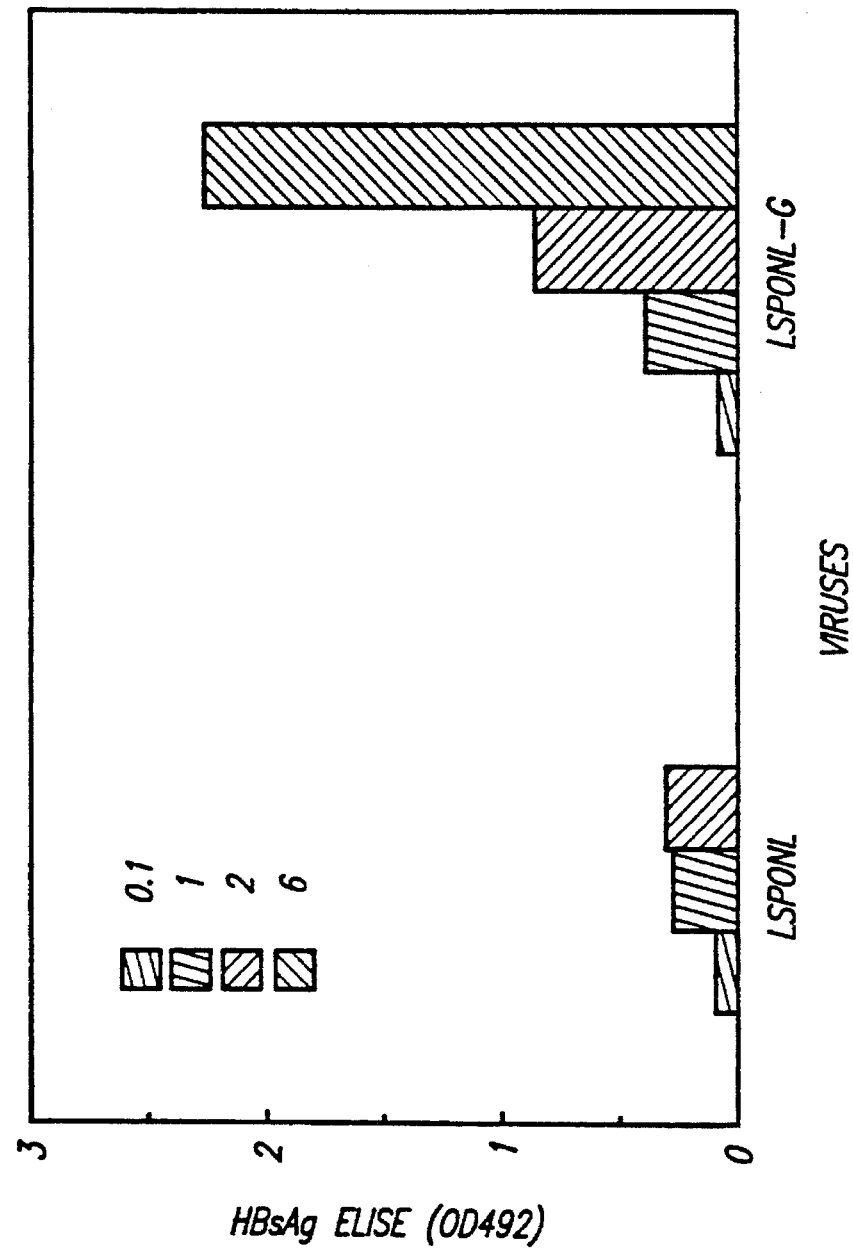
FIG. 11 depicts the level of HBsAg secreted by primary hepatocytes after exposure to different multiplicity of infection (MOI) of either LSPONL(G) or LSPONL(A).

Primary murine hepatocytes represent important target cells for gene therapy, therefore, these hepatocytes were used to determine the infection efficiency of the LSPONL(G) virus. We exposed the primary hepatocyte culture to varying multiplicity of infection (MOI) of either LSPONL(G) or LSPONL(A) virus. 3 days after infection with virus, the level of HBsAg secreted into the culture medium was determined by ELISA. As shown in FIG. 11, expression of the HBV S antigen in LSPONL(A) infected cells reached the maximum level with MOI equal to 1. In contrast, expression of the HBV S antigen in LSPONL(G) infected cells continued to increase with higher MOI, demonstrating that primary hepatocytes can be infected more efficiently by the pseudotyped LSPONL(G) virus its amphotropic counterpart LSPONL(A).

As described above in connection with Example 23, the retroviral vectors of the present invention containing the VSV-G membrane-associated protein can be concentrated to high titer. These high titers are especially important in gene therapy. Advantageously, the retroviral vectors of the present invention are produced in relatively high titers. They can be also be concentrated to obtain even higher titers. Accordingly, in a preferred embodiment, the virus produced according to the method described in Example 26 is concentrated according to the methods described in connection with Example 23. An example of concentration by ultracentrifugation is described in Example 28.

EXAMPLE 28

Quantification and Concentration of the LSPONL(G) Virus

Supernatants from the culture of host cells infected with the pHCMV-G plasmid were harvested, filtered (0.45μ), and subjected to ultracentrifugation in a Beckman Model L3-50 centrifuge in a SW 41 rotor at 40,000×g (25k rpm) at 4° C. for 90 minutes. Pre- and post-concentration titers were measured using rat 208F fibroblasts as described above.

The results of the concentration of vector particles by ultracentrifugation are shown in Table 10.

TABLE 10

| Quantification and concentration of the LSPONL virus by ultracentrifugation ||||||| 
|---|---|---|---|---|---|---|
| | Virus titer (cfu/ml)* ||| | Total virus (cfu) || % virus |
| Virus | Pre-conc. # | Post-conc. | Fold conc. | Pre-conc. | Post-conc. | recovered |
| LSPONL(G) | $8.0 \times 10^5$ | $1.0 \times 10^8$ | 125 | $2.1 \times 10^7$ | $2.0 \times 10^7$ | 95% |

*Titer determined on rat 208F fibroblasts.
Pre-con. = preconcentration, virus titer before ultracentrifugation.

As can be seen in Table 10, pre-concentration titer of the LSPONL(G) virus was already relatively high. Ultracentrifugation resulted in a 125-fold increase in virus titer with 95% recovery of infectious virus.

Thus, we have shown that a stable cell line harboring a retroviral vector of interest can be produced. This cell line can be used to generate retroviral vectors at high titers. The cell line can be maintained indefinitely because it lacks a gene encoding a toxic membrane-associated protein. As explained above in connection with Example 12, producer cell line stability problems have heretofore been very common. Many expressor cells die quickly due to the expression of toxic membrane-associated proteins. The present invention overcomes this difficulty by producing a stable cell line which can harbor a retroviral vector without expressing the toxic membrane-associated protein which causes cell death.

When retroviral vectors having the gene of interest are desired, nucleic acid encoding a membrane-associated protein is introduced into a subpopulation from the cell line, thereby initiating vector particle production. These vectors advantageously have an expanded host range that is determined by the membrane-associated protein. A further advantage of the vectors produced in accordance with the present invention is the increased efficiency of infection in human and other cells. Accordingly, the modified retroviral vector particles of the present invention can be effectively used for stable gene transfer into both mammalian and non-mammalian cells. It will be appreciated that certain variations to this invention may suggest themselves to those skilled in the art. The foregoing detailed description is to be clearly understood as given by way of illustration, the spirit and scope of this invention being interpreted upon reference to the appended claims.

What is claimed is:

1. A method for concentrating vector particles, comprising:

growing enveloped vector particles, said enveloped vector particles comprising a nucleocapsid protein from a retrovirus, a nucleic acid sequence encapsidated by said nucleocapsid protein, and vesicular stomatitis virus (VSV) G protein;

harvesting said vector particles; and pelleting said vector particles by ultracentrifugation to concentrate said vector particles.

2. The method of claim 1, further comprising resuspending said pellet in a liquid and subjecting said liquid to a second cycle of concentration.

3. The method of claim 2, wherein said liquid is selected form the group consisting of TNE and 0.1% Hank's balanced salt solution.

4. The method of claim 1, wherein said vector particles are concentrated to a titer of at least $10^8$ cfu/ml.

5. The method of claim 4, wherein said vector particles are concentrated to a titer of at least $10^9$ cfu/ml.

6. The method of claim 1, wherein said pellet retains over 50% of the colony forming units present prior to concentration 7. The method of claim 6, wherein said pellet retains over 90% of the colony forming units present prior to concentration.

* * * * *

UNITED STATES PATENT AND TRADEMARK OFFICE
CERTIFICATE OF CORRECTION

PATENT NO. : 5,512,421

DATED : APRIL 30, 1996

INVENTOR(S) : JANE C. BURNS; JIING-KUAN YEE; THEODORE FRIEDMANN

It is certified that error appears in the above-indentified patent and that said Letters Patent is hereby corrected as shown below:

In Column 28, Line 18 "role in vital" should be --role in viral--

In Column 35, Line 65, "0.1 x Hankxs" should be --0.1 x Hank's--

In Column 38, Line 22, "DNA (PC)" should be --DNA(PO)--

In Claim 3, Column 41, Line 13, "Selected form" should be --selected from--

Signed and Sealed this

Seventh Day of January, 1997

Attest:

BRUCE LEHMAN

*Attesting Officer*  *Commissioner of Patents and Trademarks*